United States Patent [19]
Uffenheimer

[11] Patent Number: 5,728,954
[45] Date of Patent: Mar. 17, 1998

[54] APPARATUS AND METHOD FOR INTEGRATED SAMPLING FROM CLOSED AND OPEN SAMPLE CONTAINERS

[75] Inventor: Kenneth F. Uffenheimer, Mahopac, N.Y.

[73] Assignee: Technicon Instruments Corporation, Tarrytown, N.Y.

[21] Appl. No.: 390,619

[22] Filed: Feb. 17, 1995

Related U.S. Application Data

[62] Division of Ser. No. 988,074, Dec. 9, 1992, which is a division of Ser. No. 671,713, Apr. 4, 1991, Pat. No. 5,201,232.

[51] Int. Cl.$^6$ ........................................ G01N 1/14
[52] U.S. Cl. ........................... 73/864.22; 73/864.24
[58] Field of Search ........................... 73/864.21–864.23, 73/864.83, 864.84, 864.87, 864.01, 864.11–864.18, 864.24; 422/100, 104, 81

[56] References Cited

U.S. PATENT DOCUMENTS

| | | |
|---|---|---|
| 3,712,794 | 1/1973 | Farr . |
| 3,960,020 | 6/1976 | Gordon et al. . |
| 4,478,095 | 10/1984 | Bradley et al. . |
| 4,713,974 | 12/1987 | Stone . |
| 4,756,201 | 7/1988 | Uffenheimer . |
| 5,149,658 | 9/1992 | Cassaday et al. . |

*Primary Examiner*—Robert Raevis
*Attorney, Agent, or Firm*—Andrew L. Klawitter; James J. Romano, Jr.

[57] ABSTRACT

Integrated sampler apparatus and method are provided and include a sample liquid container support component which is operable to support both closed and open sample liquid containers thereon on a random basis. Sample liquids from the open sample liquid containers are presented directly to a sample liquid analysis system probe for access thereby; while sample liquids from the closed sample liquid containers, which take the form of sample liquid containers closed by sample needle-pierced stoppers, are transferred by virtue of a sampling needle assembly and connected sample liquid transfer conduits and transfer valve, to a sample liquid dispensing well for access by the same sample liquid analysis system probe. Air segmented rinse liquid is provided for the sampling needle, transfer conduits, transfer valve, and dispensing well to minimize sample liquid carryover with regard to the sample liquids from the closed containers; and a surfactant is included with the rinse to lubricate the sampling needle to facilitate the piercing thereby of the closed sample liquid container stoppers and minimize the generation of sample liquid-contaminating stopper particles to use with aqueous sample and rinse liquids, hydrophobic sample liquid transfer conduits, transfer valve, and dispensing well surfaces are provided; and an isolation liquid which selectively wets those surfaces to the substantial exclusion of the aqueous sample and rinse liquids, is utilized in conjunction with the rinse liquid to further minimize sample liquid carryover. The open sample liquid containers and the dispensing well are supported at essentially the same level relative to the probe to maximize sampling accuracy thereby. A detector is provided to detect sample liquid identification as supported from the sample liquid container support component, and to differentiate between open and closed sample liquid containers for operation of the sample liquid analysis system probe in accordance therewith.

10 Claims, 11 Drawing Sheets

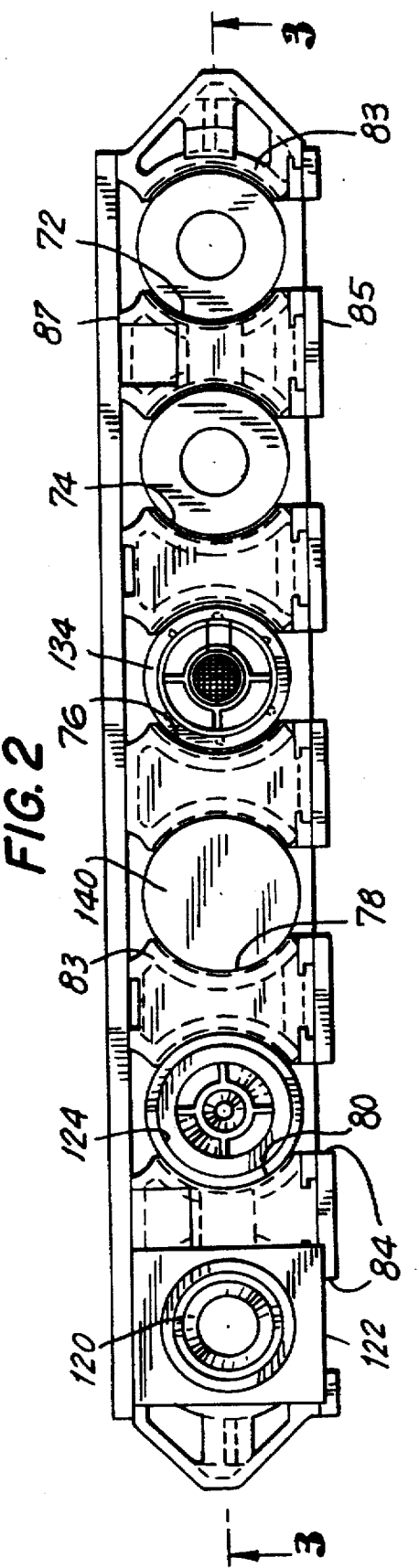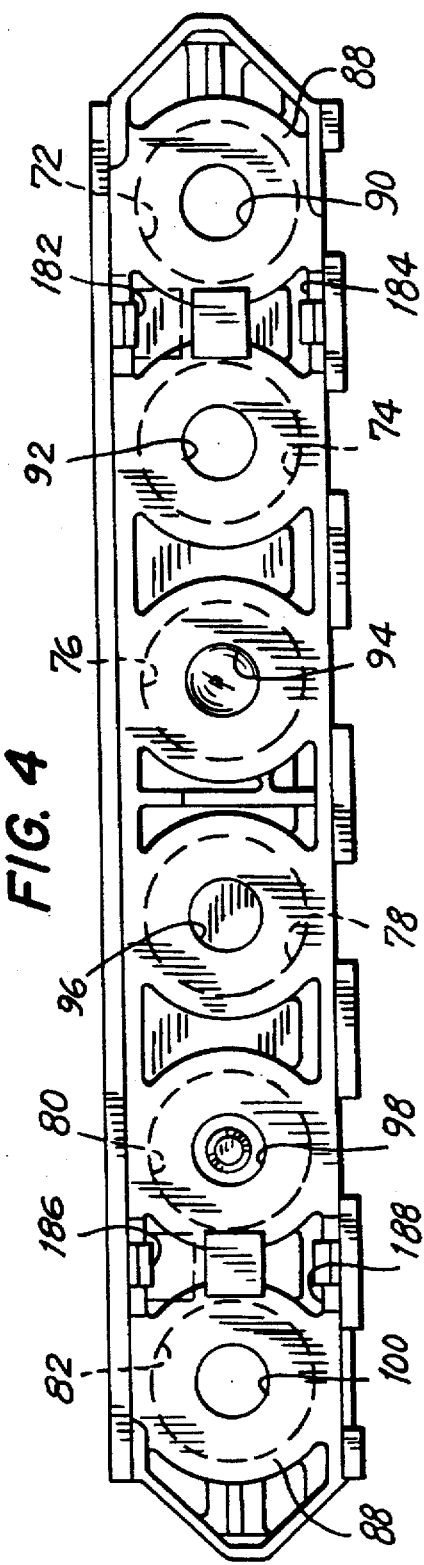

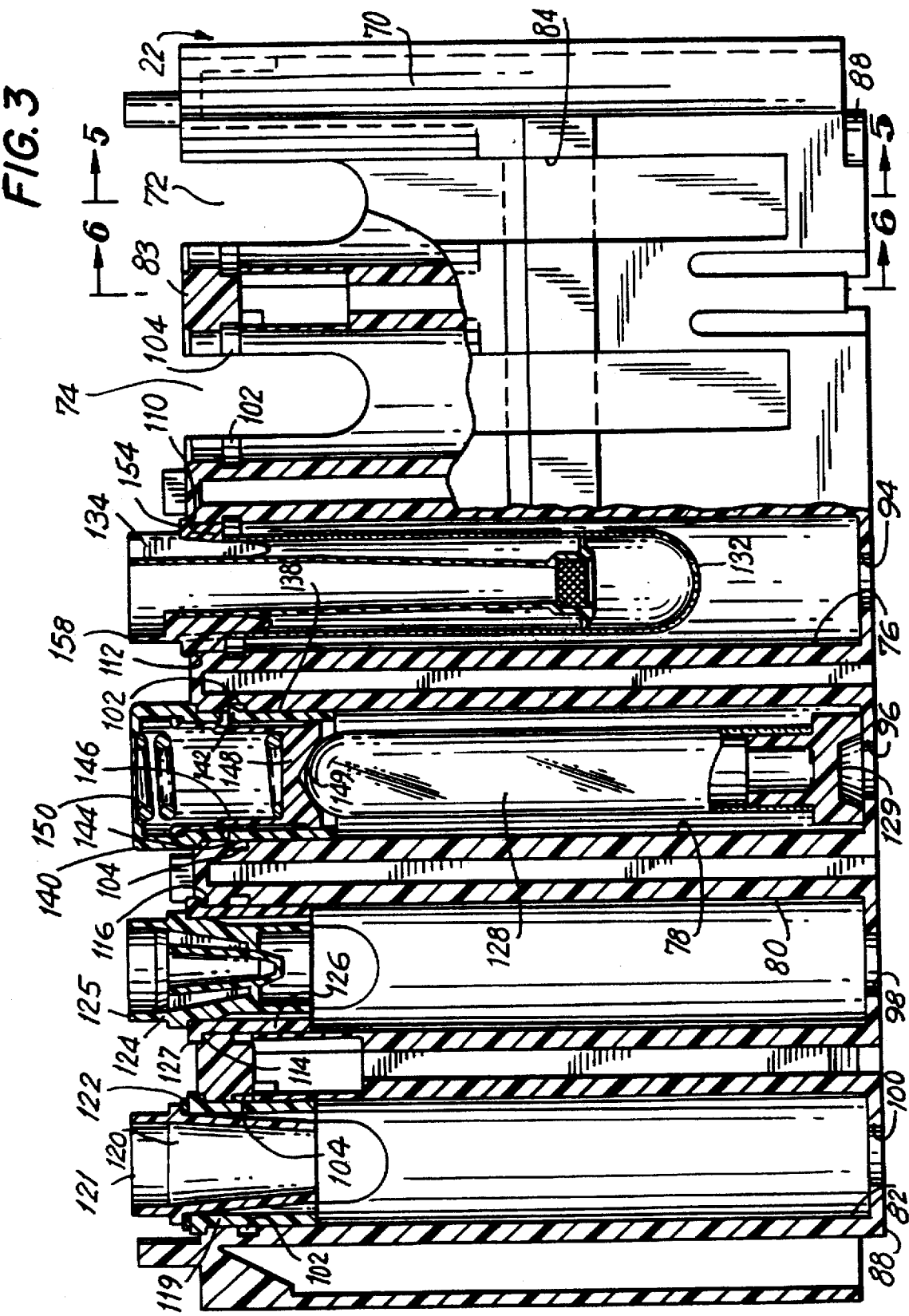

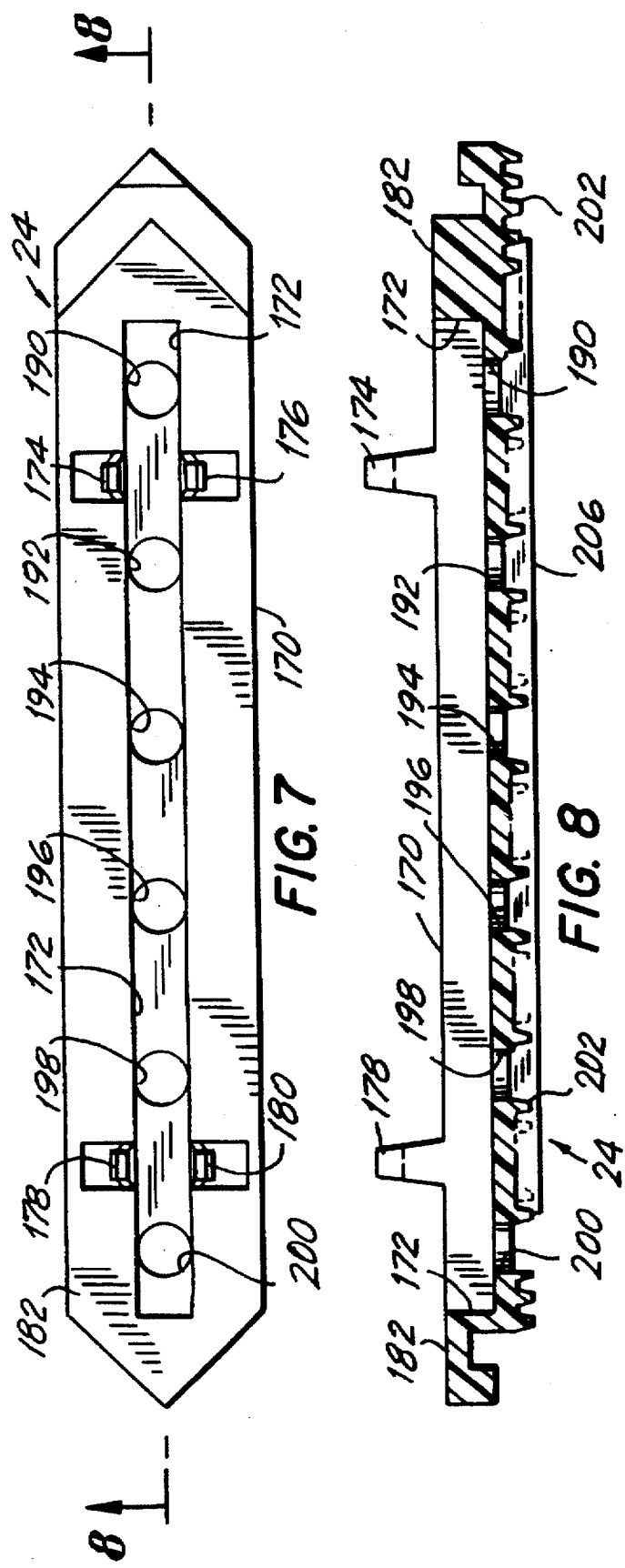

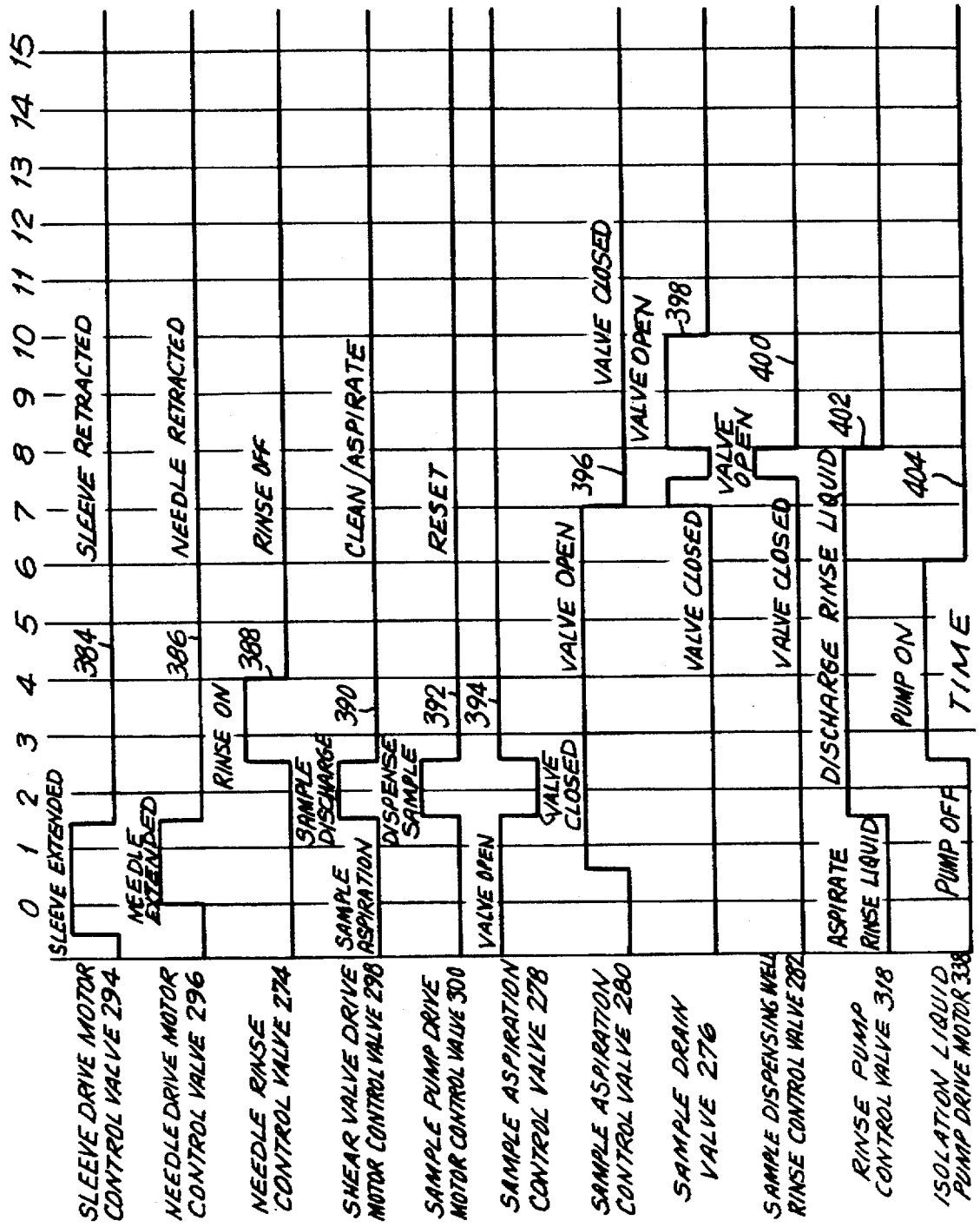

5,728,954

APPARATUS AND METHOD FOR INTEGRATED SAMPLING FROM CLOSED AND OPEN SAMPLE CONTAINERS

This application is a division of application for U.S. patent application Ser. No. 07/988,074, filed Dec. 9, 1992 by Mr. Kenneth F. Uffenheimer as a division of his application for U.S. patent application Ser. No. 07/671,713, filed Apr. 4, 1991 and now U.S. Pat. No. 5,201,232.

BACKGROUND OF THE INVENTION

1. Field of The Invention

This invention relates to new and improved apparatus and method for integrated sampling from both closed and open sample liquid containers through use of the same sample liquid analysis system sampling probe.

2. Description of the Prior Art

Although combined open and closed tube sampling is known in the prior art as disclosed in my U.S. Pat. No. 4,756,201 issued Jul. 12, 1988, and assigned to the assignee hereof, there is no teaching or contemplation in that patent disclosure of configuring or operating the combined sampler to make possible sampling from both closed and open sample liquid containers through use of the same sample liquid analysis system sampling probe; which, particularly in contemporary, high-speed and highly accurate sample liquid analysis systems, is of somewhat fragile configuration and of precisely defined and strictly limited range of high-speed travel and, as such, is totally inapplicable to sampling from closed sample containers by the piercing as required of the tube stoppers.

In addition, U.S. Pat. No. 4,756,201 representatively discloses the consistent prior art requirements for separate and distinct sample liquid container support components for the transport of closed and open sample liquid containers to and through the sampler, and for the sampling from those closed and open sample liquid containers at different sampler locations; and further requires in accordance with the principles of the prior art that the respective closed and open sample liquid containers be of essentially of the same configurations for effective support and feed thereof as above; thereby rendering impossible the totally random loading of both closed and open sample liquid containers of markedly different configurations on the same sampler support component.

Too, and although sampler component rinse to minimize sample liquid carryover, i.e. the contamination of a succeeding sample liquid by the residue of a preceding sample liquid attendant successive sample liquid analyses, and thereby maximize the accuracy of the successive sample liquid analyses results, is known in the prior art, as also clearly disclosed for example in my U.S. Pat. No. 4,756,201, as is the use of hydrophobic sample liquid analysis system components and hydrophobic isolation liquids, or "oils" which selectively "wet" those components to the substantial exclusion of aqueous sample liquids, again for the purposes of sample liquid carryover minimization, as disclosed for example in U.S. Pat. Nos. 3,479,141 and 4,253,846 to William J. Smythe, respectively issued Nov. 18, 1969 and Mar. 3, 1981, and assigned to the assignee hereof; no prior art sampler apparatus or method are known which effectively combine these two procedures to result in overall sample liquid carryover minimization to levels well below those of highly stringent contemporary clinical significance, and to result in minimization of rinse liquid consumption and sampler time required for the rinse cycle.

Also, no prior art sampler apparatus or method are known wherein a plurality of markedly different open sample liquid containers may be supported at essentially the same level from a common container support component, or wherein sample liquids from both open and closed sample liquid containers may be readily presented at essentially the same level to a sample liquid analysis system probe.

Further, although the use of a sampling needle for sampling from closed sample liquid tubes by the piercing of a tube stopper is, of course, well known in the prior art, again for example as clearly disclosed in my U.S. Pat. No. 4,756,201, no prior art sampler is known wherein a surfactant and an isolation liquid as above are applied to the sampling needle during needle rinse thereby effectively lubricating the same for the piercing of the stopper(s) of subsequently supplied closed sample tube(s) to greatly facilitate such penetration and minimize stopper particle generation, and attendant sample liquid contamination and degradation in sample liquid analysis accuracy by such particles.

In summary, it may be understood that no prior sampler or related art is known which discloses or makes obvious the hereindisclosed combinations of sampler elements and sampling steps as respectively embodied in the sampler apparatus and sampling method of my invention.

OBJECTS OF THE INVENTION

It is, accordingly, an object of my invention to provide new and improved apparatus and method for integrated sampling from closed and open sample liquid containers.

It is another object of my invention to provide apparatus and method as above which provide for sampling from both closed and open sample liquid containers through use of the same sample analysis system probe.

It is another object of my invention to provide sampler apparatus and method as above which enable the highly efficient, totally random loading and transport of both closed and open sample liquid containers through use of the same sample liquid container carrier component.

It is another object of my invention to provide sampler apparatus and method as above which, through an effective combination of sampler component rinse and, for use with aqueous sample liquids, the use of hydrophobic sampler component internal surfaces and a highly hydrophobic isolation liquid which selectively "wets" those surfaces to the substantial exclusion of aqueous sample liquids, are effective to minimize sample liquid carryover to levels previously unattainable by sampler apparatus and sampling methods.

It is another object of my invention to provide sampler apparatus and method as above which enable significant reduction in sampler rinse consumption, and the "down" or non-sample-analysis time required for the sampler rinse cycle.

It is another object of my invention to provide sampler apparatus and method as above which, with regard to sampling from closed sample liquid containers through use of a sampling needle to pierce a closed sample container stopper, provide for highly effective lubrication of the sampling needle to greatly facilitate the piercing of the container stopper by the needle, thereby minimizing sample-contaminating generation of particles of the container stopper, and maximizing the accuracy of the sample analysis results.

It is another object of my invention to provide sampler apparatus and method as above which are readily operable to present sample liquids from both closed and open sample liquid containers to the sample analysis probe at essentially the same sample liquid level, thereby maximizing the sampling accuracy of the sample analysis system probe.

It is another object of my invention to provide sampler apparatus and method as above which are readily operable to support a wide variety of markedly different open sample liquid containers at essentially the same level from a common support component to greatly facilitate the emplacement of a common evaporation cover thereover.

It is another object of my invention to provide sampler apparatus and method as above which are particularly adapted to highly satisfactory operation in conjunction with a wide variety of clinical sample analysis apparatus and methods.

It is a further object of my invention to provide sampler apparatus and method as above which require only the use of readily available materials and components of proven dependability in the fabrication thereof, and which are thus capable of long periods of satisfactory, essentially maintenance-free operation.

It is a still further object of my invention to provide sampler apparatus and method as above which are satisfactorily operable at high sampling rates fully commensurate with the high sample analysis rates of contemporary, sample analysis systems.

SUMMARY OF THE INVENTION

As disclosed herein, the new and improved apparatus and method of my invention for integrated sampling from closed and open sample liquid containers comprise a universal sample container carrier block including a plurality of spaced, sample container mounting apertures formed therein, and in each of which may be operatively mounted either a closed or open sample liquid container, thus enabling random sample liquid container loading of the carrier block. The carrier block is indexable to place each of the sample liquid containers in turn at a sampling position relative to a relatively fragile, high speed and precisely operable sample analysis system probe. Sample liquid container detector means are operatively associated with the carrier block and determine whether the container is a closed or open sample container as the same reaches the sampling position. If it is an open sample liquid container, sampling is effected directly from the container by the probe. It if is a closed sample liquid container, sample transfer means which are operatively associated with the carrier block operate to transfer sample liquid from the closed sample container to sample liquid dispensing means which are accessible by the probe for sampling therefrom. Means are provided to rinse the sample transfer and dispensing means with a rinse liquid to remove sample liquid residue therefrom, thereby minimizing the contamination of a succeeding sample liquid by that residue. In addition, and for use with aqueous sample liquids, the internal flow passages of the sample transfer and dispensing means are hydrophobic, and means are operatively associated therewith to introduce an isolation liquid thereto which selectively wets those flow passages to the substantial exclusion of the aqueous sample liquids thereby inhibiting the adherence of sample liquid residue thereto and further minimizing the contamination of succeeding sample liquids by the residues of preceding sample liquids. The closed sample liquid containers take the form of sample tubes which are sealed by pierceable stoppers, and the sample transfer means include a sampling needle which is operable to pierce those sample tube stoppers to withdraw sample liquids therefrom. Means are provided to introduce a surfactant liquid with the rinse liquid onto the sampling needle, and this operates to lubricate the same for the piercing of subsequent closed sample tube stoppers thereby minimizing the generation of tube stopper particles and the contamination thereby of the sample liquids. The universal carrier block sample container mounting apertures are configured to support all open sample liquid containers at essentially the same level relative to the carrier block; and this, in conjunction with the disposition of the sample liquid dispensing means also at essentially that same level, facilitates the presentation of all sample liquids from both closed and open sample liquid containers to the analysis sytem probe at essentially the same sample liquid level, thereby insuring a full and consistent sample "pull" for the probe of all sample liquids from each of the open and closed sample containers, with resultant maximization of the sample liquid analysis results. In addition, this facilitates the placement of an evaporation cover over a "loaded" carrier block, or group thereof, to prevent sample liquid evaporation from the open sample containers prior to sampling and analysis.

DESCRIPTION OF THE DRAWINGS

The above and other objects and significant advantages of my invention are believed made clear by the following detailed description thereof taken in conjunction with the accompanying drawings wherein;

FIG. 2 is a top plan view of the universal sample container carrier block of the sampling apparatus of FIG. 1;

FIG. 3 is a partial cross-sectional view taken generally along line 3—3 in FIG. 2;

FIG. 4 is a bottom plan view of the universal sample container carrier block of the sampling apparatus of FIG. 1;

FIG. 7 is a top plan view of the universal carrier block drive shuttle of the sampling apparatus of FIG. 1;

FIG. 8 is a cross-sectional view taken generally along line 8—8 in FIG. 7;

FIG. 9 is a bottom plan view of the drive shuttle of FIG. 7;

FIG. 16 is a timing diagram illustrating the respective operations of the control components of the sampling apparatus of FIG. 1 as drawn to the same time scale.

DETAILED DESCRIPTION OF THE INVENTION

Figure 1:
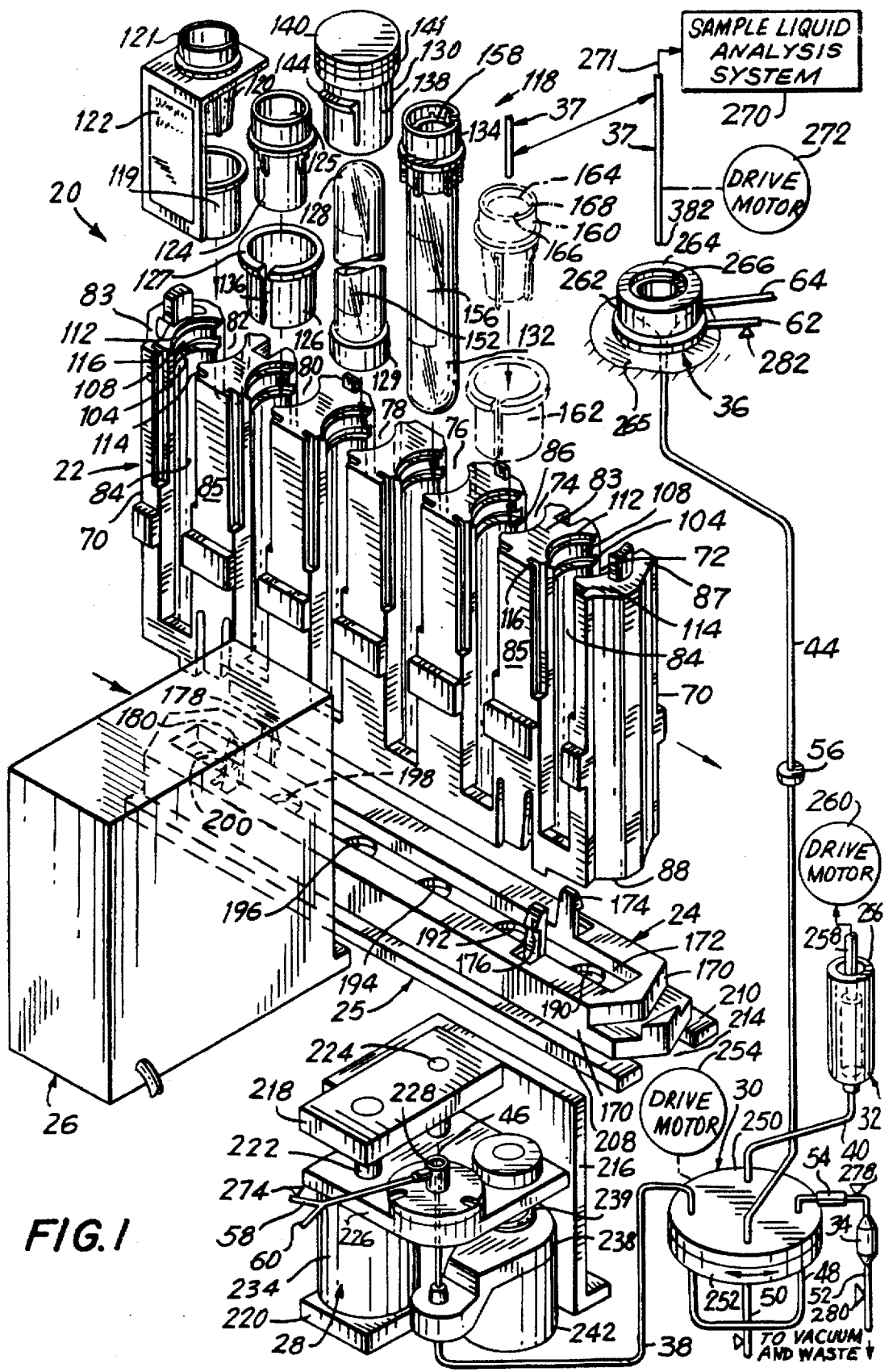
FIG. 1 is an exploded perspective view integrated closed and open sample container sampling apparatus representatively configured and operable in accordance with the teachings of my invention.
Figure 5:
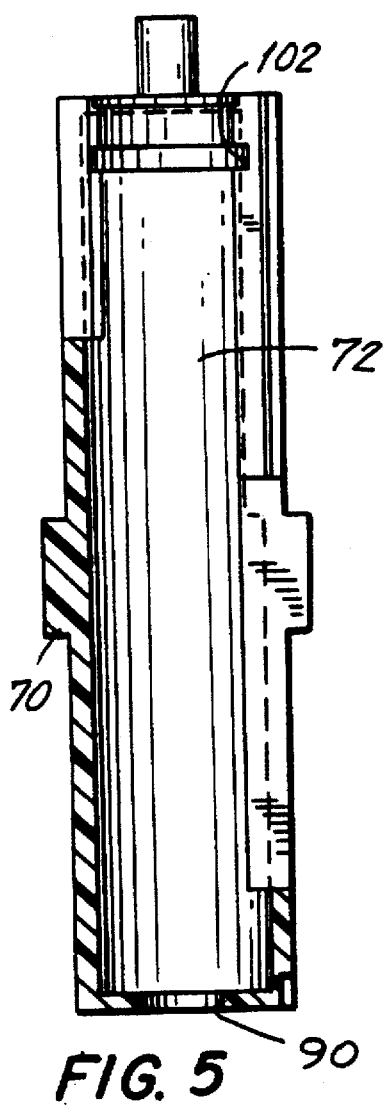
FIG. 5 is a cross-sectional view taken generally along line 5—5 in FIG. 1.
Figure 6:
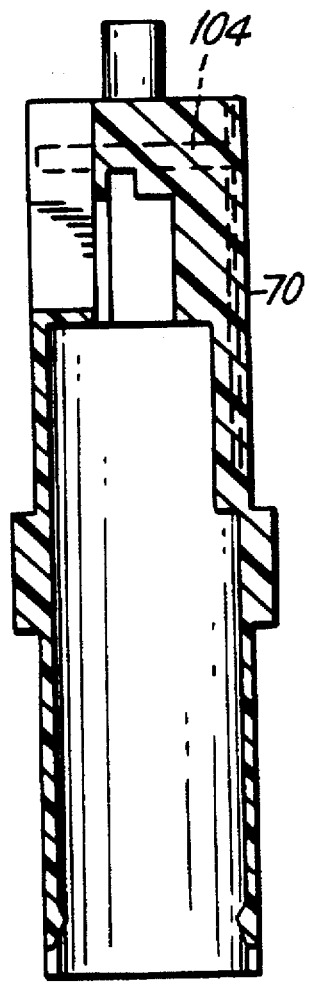
FIG. 6 is a cross-sectional view taken generally along line 6—6 in FIG. 3.
Figure 10:
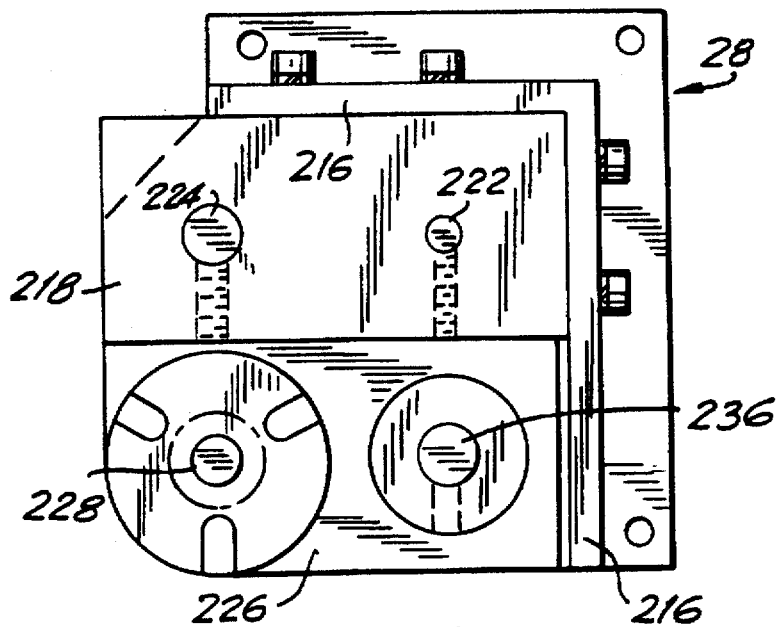
FIG. 10 is a top plan view of the sampling needle and needle drive assembly of the sampling apparatus of FIG. 1.

Referring now to the patent application drawings, an automated, integrated sampler representatively configured and operable in accordance with a best mode of the teachings of my invention for randomly sampling from both closed and open sample liquid containers through use of the same sample analysis system probe is indicated generally at 20 in FIG. 1.

Sampler 20 comprises operatively associated universal sample container carrier block as indicated generally at 22; carrier block drive shuttle as indicated generally at 24; fixed drive shuttle support member as indicated generally at 25; closed sample container and sample liquid identification detector as indicated generally at 26; closed sample container sample needle and needle drive assembly as indicated generally at 28; a multiport sampling valve as indicated generally at 30; sample pump as indicated generally at 32; closed sample container pressure equalization chamber as indicated generally at 34; an open sample aspiration well as indicated generally at 36; and a sample analysis system sampling probe as indicated generally at 37; respectively.

Flexible conduits of standard, generally inert plastic laboratory tubing, for example Teflon, are indicated at 38, 40, 42 and 44 in FIG. 1, and respectively connect the closed sample container sampling needle 46 of assembly 28, pump 32, equilibration chamber 34, and sample aspiration well 36 as shown to different ports of sampling valve 30; while a like conduit as indicated at 48 forms a volumetric loop between still different ports of the sampling valve 30. Conduits of the same configurationas above are indicated at 50 and 52 and respectively extend from sampling valve 30, and equilibration chamber 34, to vacuum and therefrom to waste, as indicated on drawing FIG. 1.

A sample liquid edge detector is indicated at 54 and is operatively disposed as shown in conduit 42 between sampling valve 30 and equilibration chamber 34, and a sample particle trap is indicated at 56 and is operatively disposed as shown in conduit 44 between sampling valve 30 and sample aspiration well 36; both for purposes described in detail hereinbelow.

Flexible rinse liquid and isolation liquid supply conduits are indicated at 58 and 60, and respectively extend from pumped sources of the same, as illustrated and described in detail hereinbelow with regard to drawing FIG. 13, into communication with sample aspiration well 36; while flexible rinse and isolation liquid supply conduits are also indicated at 62 and 64 and extend as shown from those same pumped sources into communication with the sample needle 46 in manner illustrated and described in detail hereinbelow with regard to FIGS. 12 and 13.

Referring now to FIGS. 1 through 6 of the application drawings for more detailed description of the universal carrier block 22, the same will readily be seen to comprise a generally slab-like body member 70 in which are formed as shown a plurality of equally spaced, generally identical and vertically extending universal sample container mounting apertures as indicated at 72, 74, 76, 78, 80 and 82, respectively, in FIGS. 1, 2, 3 and 4; with each of the sample container mounting apertures extending as shown through the top wall 83 of the carrier block body member 70 so as to be readily accessible from above the carrier block 22. In addition, the respective opposed side walls 85 and 87 of the carrier block body member 70 are cut-away as indicated at 84 and 86 to provide for light transmission between certain of the aperture-mounted sample containers and the detector 26 for purposes described in detail hereinbelow.

As best seen in FIGS. 3 and 4, each of the universal carrier block sample container mounting apertures extends substantially through the carrier block body member 70 from the top to the bottom thereof to terminate at the bottom wall 88 of the block; and this bottom wall is centrally pierced for each of the mounting apertures by identical, closed sample container sampling openings as shown at 90, 92, 94, 96, 98 and 100 in FIGS. 3 and 4. Aligned, arcuate mounting grooves 102 and 104 are formed as best seen in FIGS. 3 and 1 in the upper portions of the opposed wall surfaces 106 and 108 of each of the sample container mounting apertures 72, 74, 76, 78, 80 and 82; and the aligned upper extremeties of the mounting apertures are also arcuately grooved in each instance as indicated at 110 and 112 in FIGS. 3 and 1; both for purposes described in detail hereinbelow. As best seen in FIG. 1, aligned, generally vertically extending mounting slots 114 and 116 are formed in the side wall 85 of the carrier block body member 70 to either side of the cut-away portion 84 of that body member side wall for each of the apertures 72, 74, 76, 78, 80 and 82, again for purposes described in detail hereinbelow.

A respresentative array of different sample containers, and operatively associated sample container liquid identification, and sample container mounting, components, is indicated generally at 118 in FIG. 1 to clearly illustrate the particularly advantageous, universal sample container carrying capability of the carrier block 22. More specifically, representative sample container array 118 includes a standard open sample liquid cup 120 of, for example, 1 milliliter capacity, with suitably attached adapter and sample liquid identification card, as indicated at 119 and 122, respectively; a standard open sample liquid cup as above, and cup mounting adapter, as respectively indicated at 124 and 126; a standard sample liquid tube, for example a Vacutainer, closed and sealed by a readily pierceable stopper, as respectively indicated at 128 and 129, and a closed sample liquid tube retainer member as indicated at 130; and a standard open sample liquid tube as above as indicated at 132, and within which is operably disposed an automatic liquid level adjusting and filtering device as indicated at 134, and as disclosed in U.S. Pat. No. 4,602,995 issued Jul. 29, 1986 to Michael M. Cassaday, et al, and assigned to the assignee hereof. Device 134 functions to automatically adjust the level of the sample liquid in tube 132 to a predetermined, precisely repeatable level relative to tube 132 for optimal access by a sample liquid analysis system probe as described in detail in U.S. Pat. No. 4,602,995; and the disclosure of U.S. Pat. No. 4,602,995 is hereby incorporated by reference herein.

Open sample liquid cup 120, and adapter 119 and identification card 122 are operatively mounted in aperture 82 and slots 114 and 116 of the carrier block 22 by the simple insertion of the card 122 into the slots 114 and 116 for that aperture, and of the adapter 119 and 120 into aperture 82, and the downward movement of the card and cup until the card comes to rest with the cup securely supported as best seen in FIG. 3 in the carrier block 22, with the cup lip 121 at a predetermined level above the upper surface 83 of the carrier block 22. With the cup 120 and identification card 122 mounted as described in carrier block aperture 82, it will be clear that identification card will be readily "accessible" by detector 26 of FIG. 1 for positive identification of the sample liquid container in cup 120.

Open sample cup 124 is operatively mounted in carrier block mounting aperture 80 as indicated and seen in FIGS. 1 and 3 by disposing the cup in adapter 126 and inserting the resultant cup-adapter combination in the aperture from above, with the upper lip 127 of adapter 126 fitting precisely as shown in FIG. 3 into the mounting grooves 110 and 112 of the mounting aperture 80; it being noted that adapter 126, which is made for example from a resilient plastic, is of greater diameter than carrier block mounting aperture 80 and is vertically split as shown at 136 in FIG. 1. Thus, disposition as seen in FIG. 3 of the sample cup-adapter combination in mounting aperture 80 results in a particularly secure fit of the same therein due to the required compression of the resilient, split adapter 136. FIG. 3 makes clear that sample cup 124 is supported as described in carrier block mounting aperture 80 so that the cup lip 125 is at essentially the same level relative to the upper carrier block surface 83 as lip 121 of cup 120; and this, assuming cups 124 and 120 to be filled to substantially the same sample liquid level relative to the cup lips, is of particularly significant advantage with regard to insuring consistent access to the sample liquids contained in cups 120 and 124 by the sample liquid analysis system probe 37 as discussed in greater detail hereinbelow. Although not shown, it will be clear to those skilled in this art that mounting as described of the open sample cup-adapter combination 124, 126 in carrier block mounting aperture 80 in accompanied by the simple insertion of an appropriate, flat sample liquid identification card in the relevant mounting slots 114 and 116 for aperture 80 to positively identify the sample liquid contained in cup 124 to detector 26.

Stoppered, closed sample tube 128 is operatively disposed in carrier block mounting aperture 76 by the simple insertion of the tube thereinto from above with the stopper side down as indicated and seen in FIGS. 1 and 3, respectively. Thereafter, closed sample tube retainer 130—which, as best seen in FIG. 3, comprises a generally tubular body member 138 including enlarged body member cap 140 and radial projections 142 and 144, and a generally tubular retainer member 146 including lower end cap 148 slidably disposed therewithin and spring-biased downwardly by coil spring 150—is inserted into the mounting aperture 78 above the closed sample container, with concave lower surface 149 of end cap 148 in firm abutment with the bottom of tube 128, and retainer body member projections 142 and 144 extending as shown into the cut-away portions 84 and 86 of the carrier block body member side walls 85 and 87. The retainer 130 is then pushed firmly downward against the action of spring 150 until projections 142 and 144 are in vertical alignment with arcuate mounting apertuate grooves 102 and 104 of aperture 78; whereupon the retainer 130 is twisted to place those projections in those grooves and then released to firmly secure the closed sample tube 132 in the mounting aperture 78 as shown in FIG. 3. FIG. 1 makes clear that the closed sample tube 128 includes a sample liquid identification label 152 affixed to the outside thereof and identifying the sample liquid contained therein; and that the tube 128 is disposed in mounting aperture 78 of the carrier block 22 in such manner that the label 152 is in alignment with the cut-away portion 84 of the carrier block side wall 85 to insure light transmission between that identification label and sample liquid identification detector 26 thus providing for immediate "reading" of the label by the detector. Alternatively, a flat sample liquid identification card as heretofore described may be inserted in carrier block card mounting slots 114 and 116 for mounting aperture 78 to identify the sample liquid in closed tube 128; or both may be used, with only the card being "read" by detector 26. In addition, enlarged closed sample container retainer cap 140 is, for example, rendered highly light-reflective as by the affixation of a highly reflective strip 141 thereto as seen in FIG. 1, or color-coded, both, so as to be immediately discernible by the detector 26 as indicative of a closed sample container in carrier block mounting aperture 78.

Open sample tube 132, with liquid level adjusting and filtering device 134 operatively disposed therein, is operatively disposed in carrier block mounting aperture 76 by the simple insertion of the same thereinto from above until the shoulder 154 of the device 134 comes to precise rest as best seen in FIG. 3 in the arcuate mounting aperture grooves 110 and 112 to securely support both the device 134 and the tube 132 in mounting aperture 76. An identification label as indicated at 156 in FIG. 1 is affixed to open sample tube 132 and disposed as shown in alignment with the cut-away portion 84 of carrier block mounting aperture 76 for "reading" by detector 26 to positively identify the sample liquid in open sample tube 132. Again, as made clear by FIG. 3, the upper lip 158 of the sample liquid level adjusting and filtering device 132 is supported from the carrier block 22 as described at essentially the same level above the upper carrier block surface 83 as are the respective upper lips 121 and 125 of open sample cups 120 and 124.

Further included in representative sample liquid container and support component array 118 are an open micro-sample cup and cup-mounting adapter, as respectively depicted in phantom at 160 and 162 in FIG. 1. Micro-sample cup 160 is depicted as taking the form of that disclosed in U.S. Pat. No. 4,758,409 issued Jul. 19, 1988 to Kenneth F. Uffenheimer, and assigned to the assignee hereof; and, as such, automatically functions to insure that the level of a small quantity of sample liquid, for example 100 microliters, container therein is maintained precisely at the upper lip 164 of an inner sample liquid vessel 166 which is included therein as described in detail in U.S. Pat. No. 4,758,409, the disclosure of which is herein incorporated herein. Adapter 162 is of the same configuration and manner of utilization as that previously described for adapter 126; and it will thus be clear to those skilled in this art that operative mounting of the micro-sample cup-adapter combination 161–162 in carrier block mounting aperture 74 would be essentially the same as that heretofore described for the mounting of open sample cup 124 and adapter 126 in carrier block mounting aperture 80. An identification card, not shown, is inserted as previously described in card mounting slots 114 and 116 for carrier block mounting aperture 74 to positively identify the sample liquid contained in micro-sample cup 160 to detector 26.

Although not shown, it will be understood that mounting as described of the micro-sample cup 160 and adapter 162 in carrier block mounting aperture 74 results in the disposition of the upper lip 168 of the micro-sample cup 60 at precisely the same level above the upper surface 83 of the carrier block body member 70 as that depicted in FIG. 3 for open sample cups 120 and 124, and for liquid level adjusting device 134 in open sample tube 132.

Of particular advantage with regard to universal carrier block 22 is the fact that the essentially identical configurations of the respective sample container mounting apertures 72, 74, 76, 78, 80 and 82, and the full comparability of each of those mounting apertures to the operable mounting therein of either closed or open sample containers, enable the ready and convenient operable mounting of closed or open sample containers in each of those mounting apertures as described on a truly random basis; and further, without regard in each instance to the particular configuration of the sample container in question. This, of course, greatly facilitates the loading of the closed and open sample containers in the universal carrier block 22; and totally eliminates the possibility of error in such sample container loading by rendering literally impossible to put the "wrong" container in any particular carrier block sample container mounting aperture.

Figure 12:
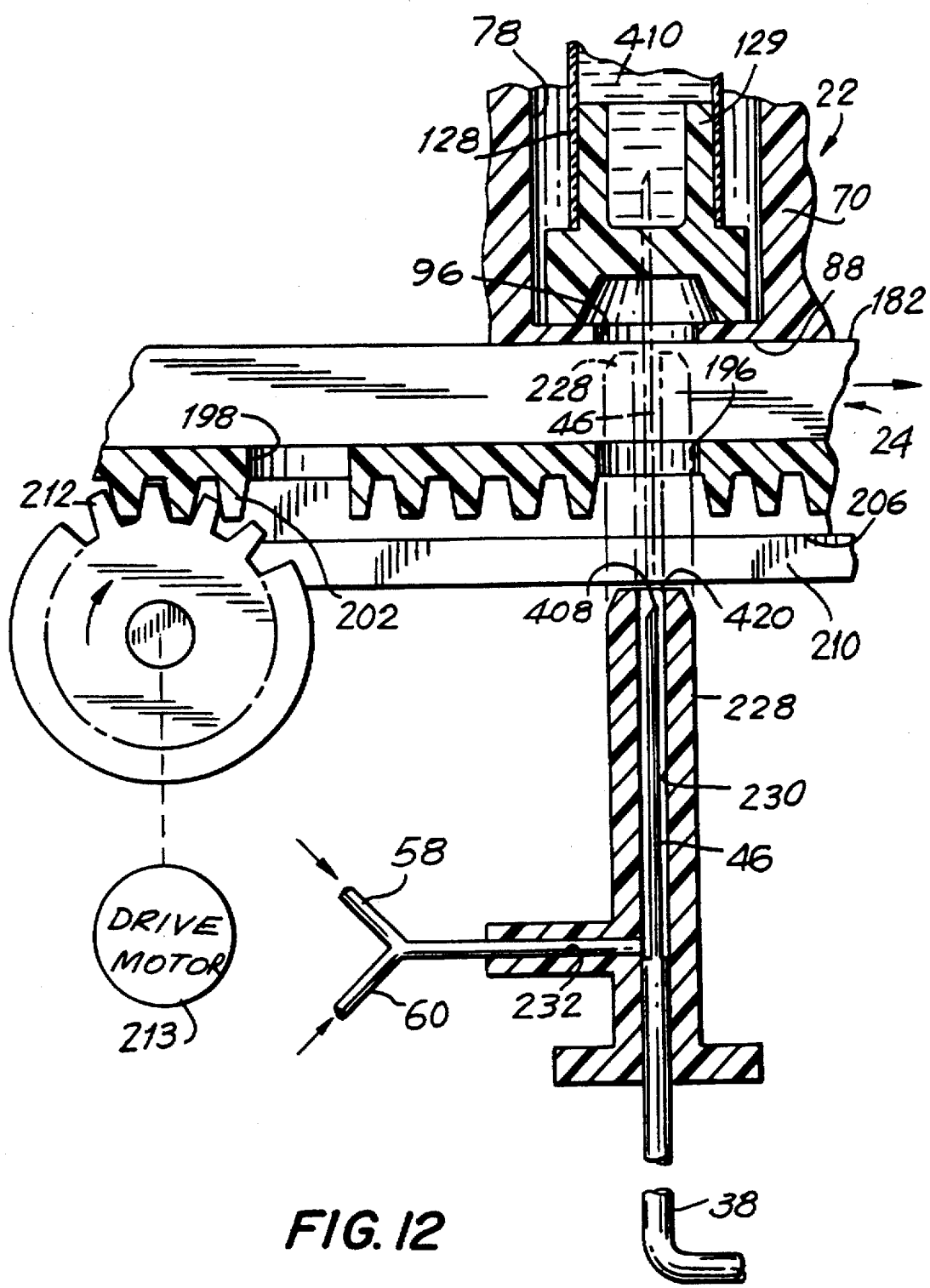
FIG. 12 is an enlarged, fragmentary cross-sectional view of the sampling needle, needle sleeve, drive shuttle, carrier block and closed sample container of FIG. 1.
Figure 13:
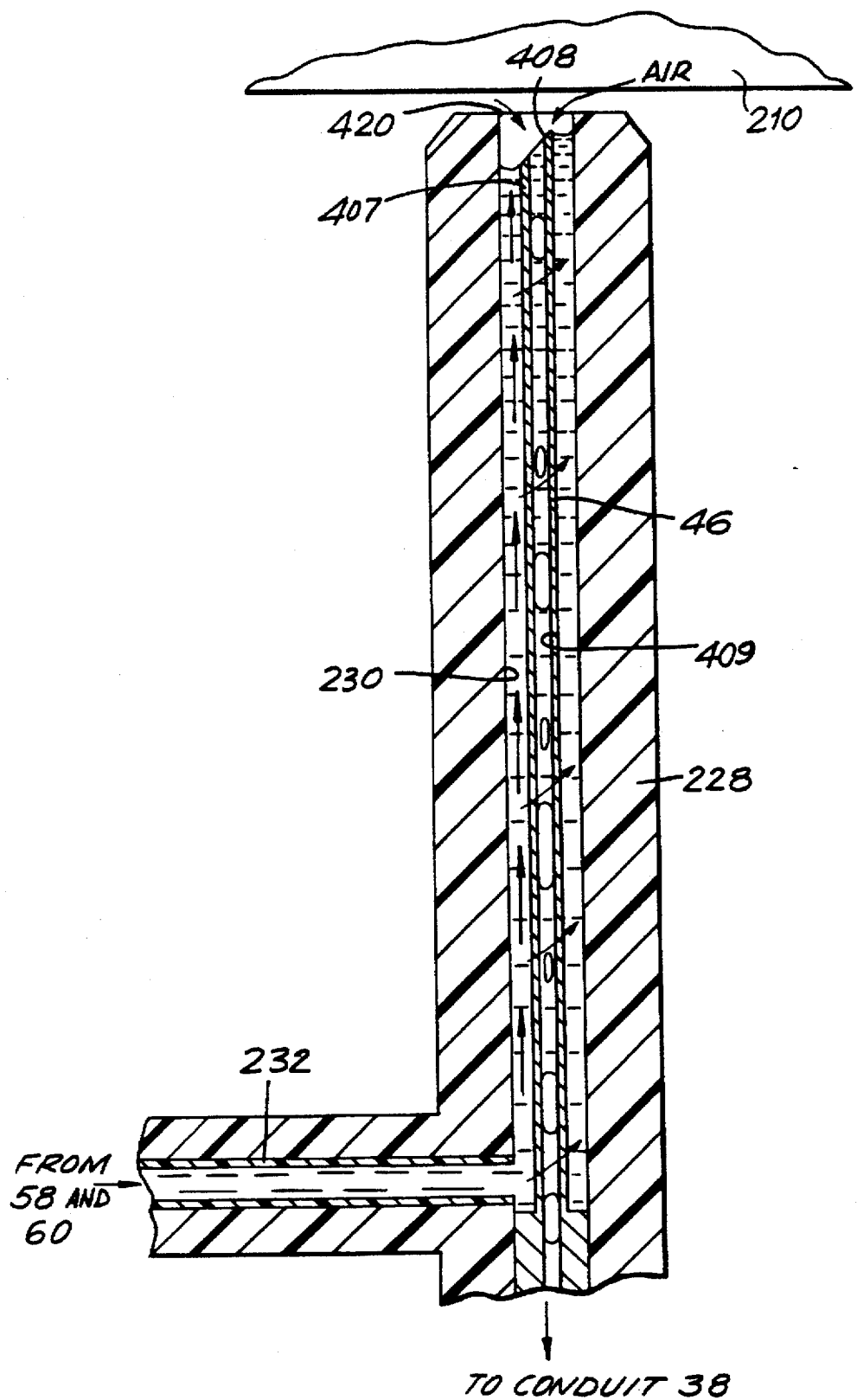
FIG. 13 is an enlarged cross-sectional view of the sampling needle and sleeve assembly of FIG. 12.

Referring now to FIGS. 1, 7, 8, 9 and 12 for more detailed description of the universal carrier block drive shuttle 24, the same will readily be seen to comprise an elongate body member 170 which is generally coextensive in length with the carrier block 22, and which includes a generally central groove 172 extending generally longitudinally thereof. Spaced, generally vertically extending drive lugs are indicated at 174, 176, 178 and 180; and extend upwardly as seen in FIGS. 1 and 8 from the upper surface 182 of the drive shuttle body member 170 into complementally configured drive slots 182, 184, 186 and 188 formed as best seen in FIG. 4 to extend through the bottom surface 88 of the universal carrier block 22, to thereby mechanically connect the drive shuttle 24 to the carrier block 22 upon the disposition of the block on the suttle with the bottom surface 88 of the carrier block 22 resting on and supported from the top surface 182 of the drive shuttle 22 as best shown in FIG. 12.

Further included in the drive shuttle 24 are spaced, closed sample container sampling apertures as respectively indicated at 190, 192, 194, 196, 198 and 200 which, upon operative disposition as described of the carrier block on the drive shuttle, will respectively align with the closed sample container sampling apertures 90, 92, 94, 96, 98 and 100 (FIG. 4) at the under surface of the carrier block 22; thereby providing immediate sampling access for the sampling needle 46 to the stopper(s) 129 of closed sample tube(s) 128 as may be disposed in any of the carrier block mounting apertures 72, 74, 76, 78, 80 and/or 82.

A generally longitudinally extending gear rack 202 is formed as best seen in FIGS. 8, 9 and 12 at the underside of the drive shuttle 24 so as to be coextensive with the drive shuttle body member 170. The rack 202 is interrupted in part as made clear in FIG. 9 by the spaced sampling apertures 190, 192, 194, 196, 198 and 200. The drive shuttle 24 further comprises spaced, longitudinally extending lower support edges 204 and 206 which extend below the rack 202 as made clear for support edge 206 by FIG. 8.

As best seen in FIG. 1, the fixed drive shuttle support member 25 comprises spaced support plates or the like 208 and 210 which extend longitudinally of the drive shuttle 24; and FIGS. 1 and 12 make clear that the drive shuttle is disposed thereon and supported therefrom by disposition of the respective drive shuttle support edges 204 and 206 on the spaced support plates 208 and 210 with freedom for slidable movement relative thereto in the direction(s) of the longitudinal drive shuttle axis.

A pinion gear is indicated at 212 in FIG. 12 and extends as shown upwardly through the space 214 (FIG. 1) between support plates 208 and 210 to drivingly mesh with the drive shuttle gear rack 202; whereby will be clear that driven rotation of the pinion 212 by operatively connected drive motor means, for example an electric drive motor as indicated schematically at 213 in FIG. 12, in the clockwise direction as indicated in FIG. 12 will be effective to slidably move the drive shuttle 24, and the operatively connected universal carrier block 22, relative to the support plates 208 and 210 to the right as indicated by the arrow in FIG. 12; it being noted in this regard that the width of the gear rack 202 as seen in FIG. 9 is sufficiently larger than the like diameters of the sampling apertures 190, 192, 194, 196, 198 and 200 to insure that the latter are not large enough to break the driving connection between the pinion 212 and the rack 202, despite the partial interruption of the rack by those apertures.

Closed sample container and sample liquid identification detector 26, which is fixedly disposed as shown in FIG. 1 adjacent the side wall 85 of the universal carrier block 22, may take the form of any two of a wide variety of readily available electro-optical devices respectively commensurate with the "reading" thereby of the various sample container identification cards and labels to positively identify the respective sample liquids contained therein; and with the detection of the enlarged cap 140 of the closed sample container retainer member 130 to alert the integrated sampler 20 of my invention to the fact that a closed sample container is operatively disposed as described in a carrier block mounting aperture of interest. More specifically, for sample liquid identification card and label reading, detector 26 may comprise a laser scanner of the nature marketed as Model #MS-500 by Microscan Systems, Inc., 939 Industry Drive, Tuckwalla, Wash. 98188; while, for detection of the highly reflective surface of strip 141 on enlarged retainer member cap 140, detector 26 may comprise a photo-electric sensing device of the nature marketed as Model #PS-46 by Keyence Corp. of America, 20610 Manhattan Place, Torrance, Calif. 90501. FIG. 1 makes clear that detector 26 is disposed immediately adjacent the universal carrier block 26 essentially in line with sample analysis system prove 37 for reasons set forth in detail hereinbelow.

Referring now to FIGS. 1, 10, 11, 12 and 13 for more detailed description of the closed sample container sampling needle and needle drive assembly 28, the same will readily be seen to comprise a vertically extending, generally L-shaped fixed support bracket 216 disposed below fixed drive shuttle support plates 208 and 210, and comprising spaced support plates 218 and 220 affixed thereto and extending perpendicularly thereof. Spaced support shafts 222 and 224 extend vertically between support plates 218 and 220; and a needle sleeve support bracket 226 is slidably mounted on those support shafts with freedom for vertical movement relative thereto. A tubular sampling needle sleeve 228, comprising a central sampling needle bore 230 (FIG. 12), and a connected rinse and isolation liquid supply bore 232 extending perpendicularly to bore 230, is fixedly attached to the upper surface of support bracket 226 and extends vertically upward therefrom as shown. A sleeve drive motor is shown at 234 in FIG. 11, and is supported from support shaft 222. Sleeve drive motor 234 may take any suitable form, for example a valve controlled, double-acting pneumatic drive motor, and is operable to drive sleeve support bracket 226, and sleeve 228, between the retracted sleeve position as shown in solid lines in FIG. 12, and the extended sleeve position as shown in phantom in FIG. 12.

Figure 11:
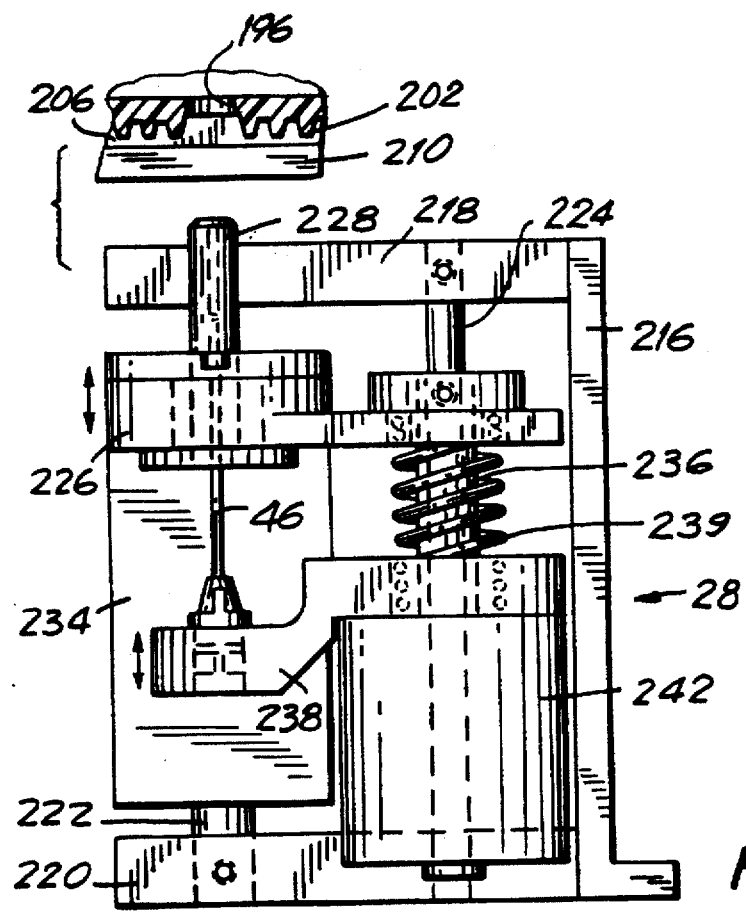
FIG. 11 is a side plan view of the assembly FIG. 10.

A support shaft is indicated at 236 in FIG. 11, and extends vertically downward of and is fixedly supported from sleeve support bracket 226. A sampling needle support bracket is indicated at 238 and is slidably support from shaft 236 with freedom for vertical movement relative thereto. Bracket 238 is spring-biased as best seen in FIG. 11 away from bracket 226 by a coil spring 239. Tubular sampling needle 46 is supported as shown from bracket 238 to extend vertically upward therefrom through sampling needle bore 230 in tubular sleeve 228. A sampling needle drive motor, again for example taking the form of a valve-controlled, double-acting pneumatic drive motor, is indicated at 242 in FIG. 11, and is supported from shaft 236. Drive motor 242 is operable independently of sleeve drive motor 234 to drive sampling needle support plate 238, and sampling needle 46, between the retracted sampling needle position as shown in solid lines in FIGS. 12 and 13, and the extended sampling needle position as shown in phantom in FIG. 12. Conduit 38 is operatively connected to the sampling passage, not shown, in tubular sampling needle 46 as indicated in FIG. 12.

Closed sample container sampling valve 30 preferably takes the form of a conventional, two-way, multi-port shear valve having a fixed upper (at least as seen in FIG. 1) valve body member 250, and a mating, lower valve body member 252 rotatable relative thereto as indicated by the arrow in FIG. 1 by a suitable drive motor, again for example a valve-controlled, double-acting pneumatic motor as indicated schematically at 254 in FIG. 1. A shear valve of this nature is disclosed in U.S. Pat. No. 4,756,201 issued Jul. 12, 1988 to Kenneth F. Uffenheimer, and assigned to the assignee hereof; and the disclosure of U.S. Pat. No. 4,756,201 is hereby incorporated by reference herein.

Valve body member 252 is rotatable by drive motor 254 relative to valve body member 250 between the position thereof depicted in FIG. 1 wherein the valve connects conduits 38 and 42 through volumetric loop conduit 48, and conduit 44 to conduit 50; and a non-illustrated valve body member position wherein the valve connects conduit 40 to conduit 44 through the volumetric loop conduit 48; all for purposes described in detail hereinbelow.

Equilibration chamber 34 is of the same configuration and manner of operation as disclosed for the like component in U.S. Pat. No. 4,756,201.

Sample pump 32 is a highly accurate, positive displacement pump taking, for example, the form of a standard syringe pump, and comprising a pump cylinder 256, and a pump plunger 258 extending therefrom. A suitable drive motor, again for example a valve-controlled, double-acting pneumatic drive motor, is shown schematically at 260 in FIG. 1, and is operatively connected as indicated to syringe pump plunger 258 to operate the pump.

Sample liquid dispensing well 36 comprises a vertically oriented, generally cylindrical body member 262 taking the general form of a container having a frusto-conical bore 264 formed therein and connected as shown at the bore bottom to conduit 44. As annular inlet groove as indicated at 266 is formed as shown in body member 262 at the upper portion of bore 264; and flow passages, not shown, are formed in the body member 262 connecting the respective rinse and isolation liquid supply conduits 62 and 64 to inlet groove 266 for the supply of those liquids to groove 266, and the downward flow therefrom under the force of gravity over the entire-surface of bore 264 to conduit 44. Although not made clear by FIG. 1, it may be understood that dispensing well 36 is fixedly disposed relative to carrier block 22 so that the upper lip 267 of the dispensing well is at essentially the same level as the respective upper lips of the open sample container disposed thereon as described hereinabove. Dispensing well 36 is supported at that level by any appropriate support means as indicated schematically at 265 in FIG. 1. A container of this general nature is disclosed in detail in U.S. Pat. No. 4,865,993 issued Sep. 12, 1989 to Michael M. Cassaday and assigned to the assignee hereof.

Sample analysis system probe 37 may take any form appropriate to the successive insertions of the same into, and the withdrawals in turn of like quantities of sample liquids from, the respective open sample containers mounted as mounted in detail hereinabove in universal carrier block 32 as the block is indexed past the probe, or from the sample dispensing well 36, all as described in detail hereinbelow; and the successive supply of the thusly withdrawn sample liquids in turn in conventional manner to an operatively associated, automated sample liquid analysis system as indicated schematically at 270 in FIG. 1, and to which probe 37 is operatively connected by an appropriate flexible conduit as indicated schematically by line 272. To this effect, probe 37 is moveable under the control of a probe drive motor as indicated schematically at 272 in FIG. 1, between the respective depicted positions of the probe wherein the same is disposed precisely above the center of a relevant open sample container on the universal carrier block 22, and precisely above the center of the dispensing well 36, respectively; and is further reciprocable from those positions into and out of the sample liquids contained in those open sample containers or the dispensing well, as the case may be, to precisely equal extents and for precisely equal periods of time, thereby insuring that precisely equal quantities of sample liquid are withdrawn therefrom by the probe 37 for supply in turn to the sample liquid analysis system 270.

Under these circumstances, it will be clear to those skilled in this art that probe 37 is, of necessity, of somewhat fragile configuration and, in any event, totally inapplicable to direct sample from a closed sample container such as tube 128 by the piercing as required of the tube stopper 129. In addition, it will be clear that, for use in contemporary, particularly high speed and highly accurate automated sample liquid analysis systems, probe 37 is strictly limited in resident aspiration time in each of the sample liquid containers, and stricly limited in terms the accelerations which can be impressed upon the probe, and the velocities at which the probe can be moved, whenever the probe is to any extent immersed in a sample liquid, or contains the same, in order to insure that at least precisely the same amount of sample liquid is aspirated by the probe and supplied in each instance to the sample liquid analysis system 270; all in the interests of the maximization of the accuracy of the successive sample liquid analysis results as described in some detail in my U.S. Pat. No. 4,758,409. Thus, it becomes of significant advantage to sample liquid analysis accuracy that all open sample containers of any nature as operatively mounted in universal carrier block 22, and the dispensing well 36, be disposed at essentially the same level relative to probe 37; thereby greatly facilitating the "filling" thereof to essentially the same sample liquid level in each instance, and maximizing the accuracy of the sample liquid analysis results. As discussed hereinabove, this is automatically accomplished by micro-sample cup 160, and by liquid level adjusting device 134 in open sample liquid tube 132, which automatically fill to the same level; and, with regard to dispensing well 262, is automatically accomplished by virtue of the retention in volumetric loop conduit 48 of precisely the same sample liquid volume from each of the closed sample liquid tubes 128 for supply in turn as described to the dispensing well. For open sample liquid cups 120 and 124, this is accomplished by the "filling" thereof with sample liquids to essentially the same level in each instance relative to the upper cup lips 121 and 125. A representative, automated sample liquid analysis system probe for use as disclosed in conjunction with the integrated sampler 20 of my invention, and one which advantageously incorporates the use of an appropriate isolation liquid for purposes of minimization of sample liquid carryover as described, is disclosed in U.S. Pat. No. 4,121,466 issued Oct. 24, 1978 to Allen Reickler, et al, and assigned to the assignee hereo; and the disclosure of U.S. Pat. No. 4,121,466 is hereby incorporated by reference herein.

An additional advantage of significance provided for by the disposition as described of all open sample liquid containers at essentially the same level relative to the upper surface 83 of the universal carrier block 22 resides in the fact that this greatly facilitates the placement of a common evaporation cover, not shown, over a "loaded" carrier block, or group thereof, to prevent sample liquid evaporation from the open containers while the same are awaiting presentation in turn to the sample liquid analysis system probe 37 for sampling; and this would be of particular advantage with regard to evaporation prevention from the small quantities of sample liquids as contained in the micro-sample cups 160.

Sample liquid edge detector 54 may take the form of an electrical conductivity detector as disclosed in U.S. Pat. No. 4,756,201 which is operable to detect the passage of the leading edge of a sample liquid through conduit 42 on the basis of the resultant change in electrical conductivity across the conduit, and to generate and output an electrical conductivity across the conduit, and to generate and output an electrical signal indicative. Alternatively, and in instances wherein conduit 42 is light-transmittive, detector 54 may be of electro-optical configuration.

Sampler particle trap 56 takes the form of a filter of pore size or mesh size appropriate to the trapping of all particultate matter above a predetermined size as may be contained in the sample liquids flowed therethrough in the direction of dispensing well 36.

Suitable valves, for example standard normally open solenoid controlled pinch valves are depicted schematically at 274, 276, 278, 280 and 282 in FIG. 1; and are respectively operatively associated as shown with conduits 58, 50, 42 (to both sides of equilibration chamber 34), and 60, to control liquid flow therethrough as described in detail hereinbelow.

With regard to materials, universal carrier block 22 and drive shuttle 24 are preferably injection molded from high strength plastics; closed sample container sampling needle preferably machined from particularly high-strength steel, needle drive assembly 28 in general machined from any appropriate metal with the exception of sleeve 228 which is preferably an injection molded plastic. Shear valve body members 250 and 252 are preferably formed and machined from appropriate, high strength ceramics. Dispensing well 36 is a machined plastic; while syringe pump 32 comprises a glass cylinder and plastic tipped, metal plunger. Equilibration chamber 34 is formed from drawn glass tubing. All system conduits are preferably of conventional, generally inert transparent laboratory plastics.

For use of the integrated sampler 20 of my invention with aqueous sample liquids, and a suitable isolation liquid to minimize sample liquid carryover and maximize the accuracy of the sample liquid analysis results as described in greater detail hereinbelow, it will be understood that the sleeve 228, conduit 38, the operative surfaces of the non-illustrated internal passages in sampling valve 30 which connect conduit 38 to volumetric loop conduit 48 and the latter to conduit 44, conduit 44, and dispensing well 36 are made or surface coated as the case may be from selected ones of a range of readily available, inert and highly hydrophobic ones of a range of readily available, inert and highly hydrophobic solid materials such as fluorinated or perflourinated hydrocarbons of low surface energy and proven chemical stability, for example, Teflon; while the isolation liquid is preferably constituted by any one of a range of fluorinated or perflourinated, highly hydrophobic liquids which are also inert and chemically stable, and which also exhibit low surface tension and appropriate viscosity; it being clear that such isolation liquid will preferentially "wet" to a marked degree those solid fluorinated or perflourinated hydrocarbon materials to the very substantial exclusion of the aqueous sample liquids. Nonlimitative examples of these solid and liquid hydrocarbons are polytetrafluoroethylene and perfluorodecalin, respectively.

With the relevant components of my integrated sampler 20, and the isolation liquid, constituted as described materials-wise, it will be clear that the provision of an extremely thin layer of the isolation liquid in manner described in detail hereinbelow on the internal surfaces of those sampler components, concomitantly with the flow of the sample liquids over those surfaces will result in that isolation liquid layer preferentially "wetting" or adhering to those surfaces to the substantial exclusion of the sample liquids; thereby very greatly inhibiting, if not totally preventing, sample liquid carryover, namely the contamination of a succeeding sample liquid by the residue of a preceding sample liquid, with attendant, and contemporarily unacceptable, degradation in the accuracy of the sample liquid analysis results. This is of particular significance in, for example, contemporary clinical analyzers wherein highly accurate sample liquid analysis results down to sample liquid constituent levels of 1 part per 100,000 or less are absolutely required.

Figure 14:
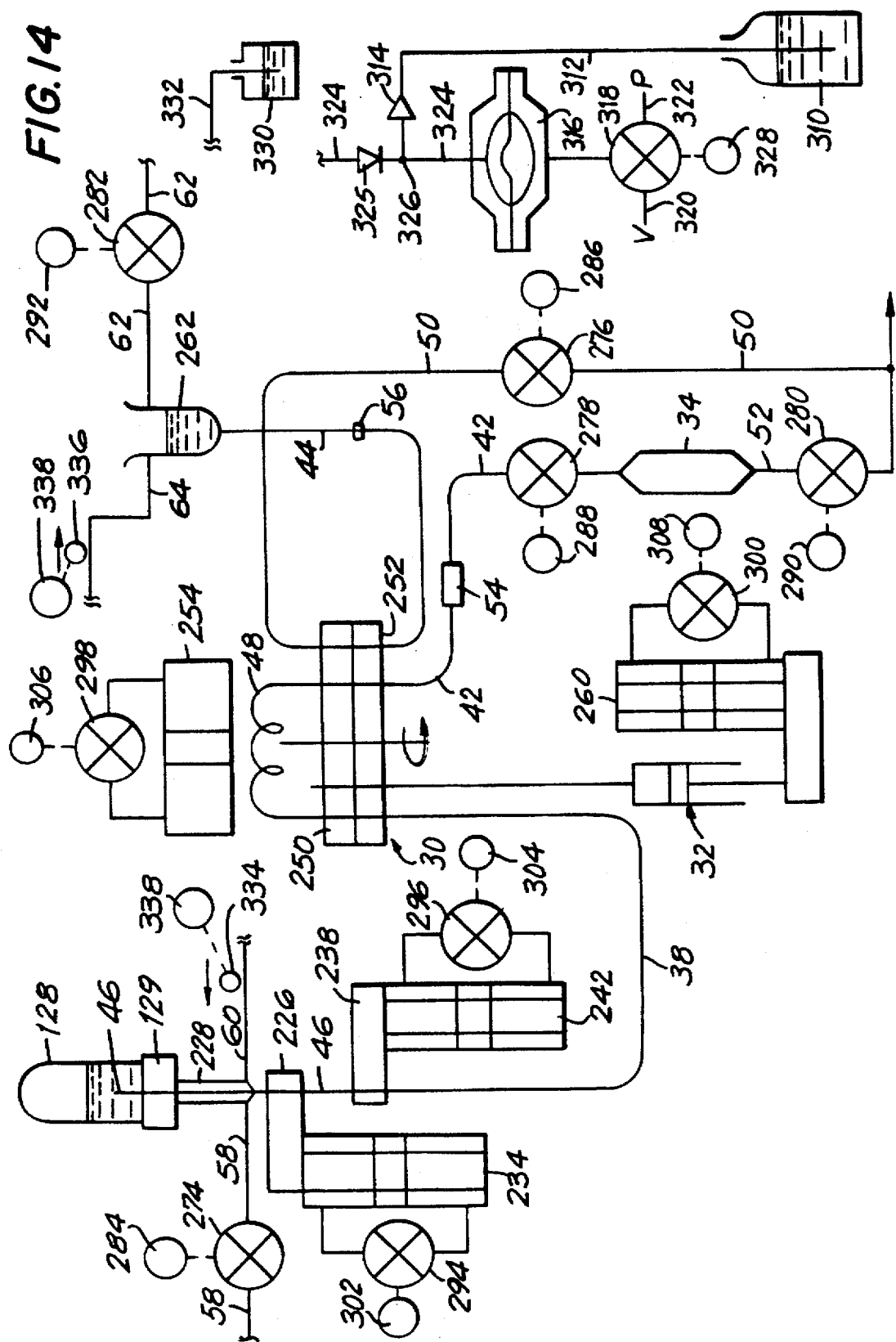
FIG. 14 is a flow diagram for the sampling apparatus of FIG. 1.

Referring now to the schematic flow diagram of FIG. 14, the same clearly illustrates the control of pinch valves 274, 276, 278, 280 and 282 by solenoids as schematically indicated at 284, 286, 288, and 292, respectively.

Four way valves are schematically depicted at 294, 296, 298 and 300 in FIG. 14; and are respectively operably connected as indicated in the pressurized fluid supply conduits of double acting pneumatic drive motors 234, 242, 254 and 260; and to a standard, non-illustrated source of pressurized fluid, for example air, to control the respective operations of those drive motors. Drive motor valve control solenoids are schematically depicted at 302, 304, 306 and 308 in FIG. 14; and are respectively operatively connected as indicated to valves 294, 296, 298 and 300 to control the operations thereof, and thus of the drive motors 234, 242, 254 and 260; thereby controlling at any point in time the respective positions of the sampling needle sleeve 228, the sampling needle 46, the lower body member 252 of sampling valve 30, and plunger 258 of syringe pump 32 in pump cylinder 256.

An open source of a suitable rinse liquid, which contains a surfactant to lubricate sampling needle 46 and thereby facilitate penetration thereby of closed sample container stopper 129 as described in detail hereinbelow, is indicated at 310 in FIG. 14; and a supply conduit 312, including check valve 314, extends thereinto as shown. A vacuum-operated diaphragm pump is depicted schematically at 316, and is operated as shown by a three-way, normally closed control valve 318 to which are connected a source of vacuum V as indicated on line 320, and a source of pressurized fluid P on line 322. Pumping conduit 324 extends as shown from pump 316 and includes a check valve 325; and conduit 312 joins with conduit 324 as indicated at 326 upstream of the valve. A valve control solenoid is indicated schematically at 328 in FIG. 14, and is operatively connected as indicated to valve 318 to control the operation thereof, and thus of pump 316. As shown, pumping conduit 324 is connected through valves 274 and 282 to rinse liquid supply conduits 58 and 62 for supply of rinse liquid therethrough to passage 230 in sampling needle sleeve 228, and bore 264 of dispensing well 36, respectively.

A source of a suitable isolation liquid as above, or "oil" as the same has now come to be commonly termed in this art, is indicated schematically at 330 in FIG. 14, and an isolation liquid supply conduit 332 extends thereinto as shown. Conduit 332 connects as indicated with each of conduits 60 and 64; and respective pump rollers of a conventional peristaltic pump as indicated schematically at 334 and 336 are operatively associated as shown with conduits 60 and 64 to pump liquids therethrough. A peristaltic pump electric drive motor as shown schematically at 338, and operates as indicated to drive pump rollers 334 and 336 to thereby provide precisely predetermined and extremely small quantities of the isolation liquid from source 330 to sleeve passage 230 and dispensing well bore 264 upon drive motor actuation.

Figure 15:
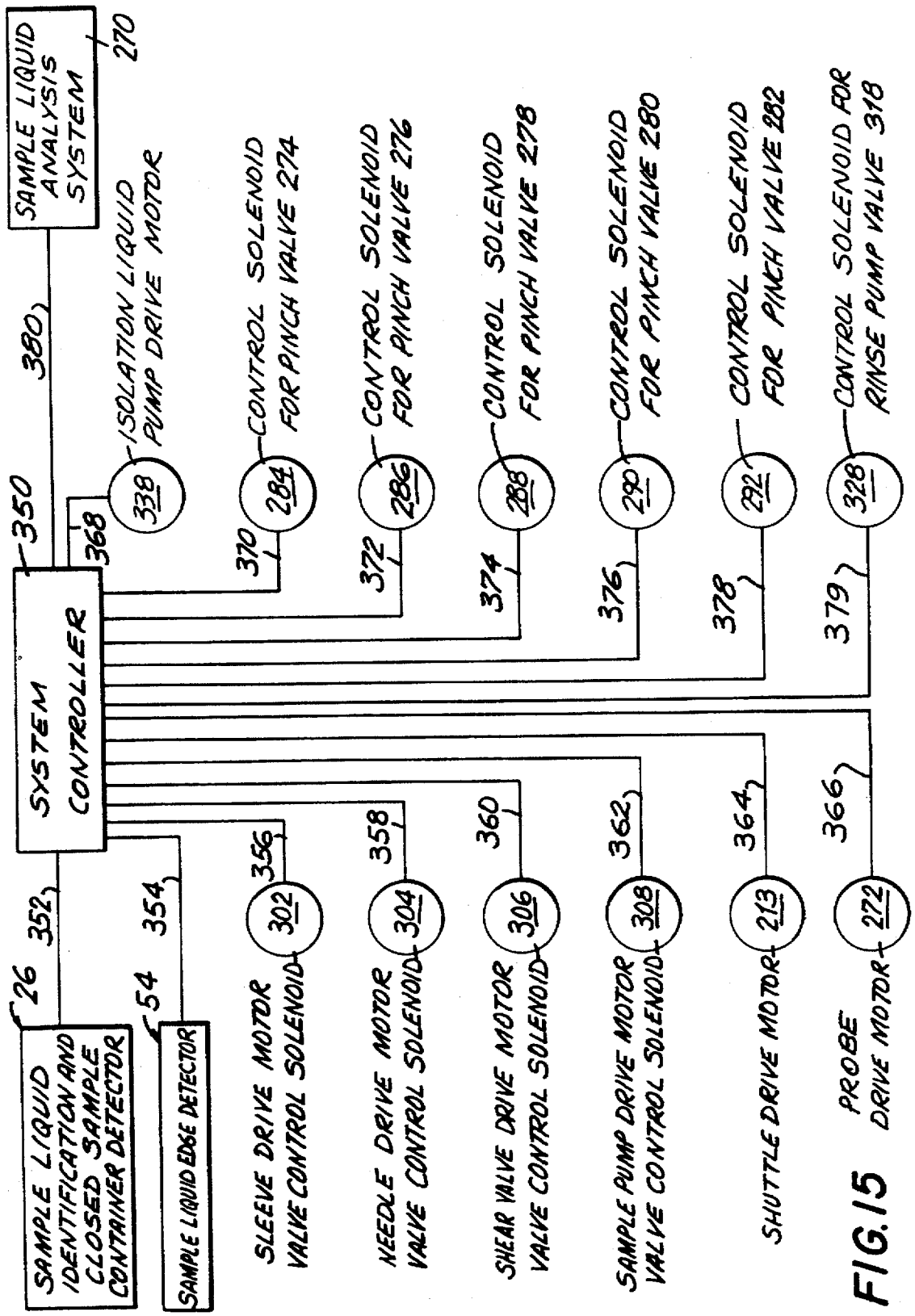
FIG. 15 is a schematic diagram illustrating the electrical control and synchronization circuit for the sampling apparatus of FIG. 1.

Referring now to the schematic circuit diagram of FIG. 15, a system controller taking, for example, the form of an appropriately programmed micro-processor or like device, is depicted schematically at 350; and is operatively electrically connected as indicated to all electrically powered components of the integrated sampler 20 of my invention, and to the sample liquid analysis system 270 to which sample liquids are to be supplied in turn by that sampler, to control and synchronize as required the respective operations thereof. More specifically, system controller 350 is electrically connected as indicated by lines 352 and 354 to detectors 26 and 54, respectively, and is electrically connected as indicated by lines 356, 358, 360 and 362 to solenoids 302, 304, 306 and 308 to input control signals thereto to control and synchronize the respective operations of the sleeve drive motor 234, the needle drive motor 242, the sampling valve drive motor 254, and the sample pump drive motor 260; thereby controlling and synchronizing the respective operations of the sleeve 228, the sampling needle 46, the sampling valve 30 and the sample pump 32.

Lines 364 and 366 electrically connect system controller 350 to shuttle drive motor 213 and probe drive motor 272 to control and synchronize the respective operations of the drive shuttle and 24 and the sampling probe 37; while lines 368 and 370 electrically connect the controller 350 to isolation liquid pump drive motor 338, and the control solenoid 328 for rinse liquid pump drive motor control valve 318 to thereby control and synchronize the respective operations of the isolation liquid peristaltic pump rollers 334 and 336, and the rinse liquid pump 316. Controller 350 is also electrically connected as indicated by lines 370, 372, 374, 376 and 378 to control and synchronize the respective operations of the pinch valve control solenoids 284, 286, 288, 290 and 292; thereby controlling and synchronizing the supply of rinse liquid to the sleeve passage 230, the drain of sample and rinse liquids by vacuum to waste through conduit 50, the connection of the equilibration chamber 34 to the sampling needle 46 for pressure equilibration of the closed sample container 128 as described in detail hereinbelow, the connection of the equilibration chamber 34 to vacuum and waste for the drain of excess sample liquid therethrough, and the supply of the rinse liquid to dispensing well 36, respectively. System controller 350 is also electrically connected as indicated by line 380 to the sample liquid analysis system 270 to synchronize and control the operation of the integrated sampler 20 of my invention in accordance with the operation of that sample liquid analysis system, and vice versa.

The timing diagram of FIG. 16 illustrates the operational conditions of the indicated components of the integrated sampler 20 of my invention as drawn to the same time scale. More specifically, in FIG. 16 waveforms 384, 386, 388, 390 and 392 respectively illustrate the operational conditions of sampler valves 294, 296, 274, 298 and 300; while waveforms 394, 396, 398, 400 and 402 respectively illustrate the operational conditions of sampler valves 278, 280, 276, 282 and 318. Waveform 404 illustrates the operational condition of isolation liquid pump drive motor 338.

In operation of the integrated sampler 20 of my invention for sampling by probe 37 from an open sample container, for example micro-sample cup 160 in universal carrier block mounting aperture 74, it will be clear that as the carrier block 22 is indexed under control of system controller 350 by driven movement as described of drive shuttle 24 by drive motor 213 to place cup 160 in "sampling" position relative to probe 37, the probe is actuated by drive motor 272 via system controller 350 to move downwardly from the retracted position thereof as illustrated in FIG. 1 to the non-illustrated extended position thereof to immerse the inlet end 382 of the probe in the sample liquid contained in cup 160 for a precisely predetermined period of time to aspirate a precisely predetermined sample liquid quantity therefrom for supply to sample liquid analysis system via conduit 271; whereupon the probe is removed from that sample liquid and cup 160, and returned to the illustrated retracted position thereof. Concomitantly, the identification data for the sample liquid contained in micro-sample cup 160 as appears on the non-illustrated sample liquid identification card operatively disposed as heretofore described in mounting slots 114 and 116 for carrier block mounting aperture 74 is "read" by sample liquid identification detector 26 and outputted to system controller 350 on line 352 for supply in turn by the controller to the sample liquid analysis system 270 on line 380 to insure exact correlation between that sample liquid and the analysis results therefor.

Since micro-sample cup 160 is an open sample container and, as such, does not include an enlarged cap 140 with reflective strip 141, no signal indicative of a closed sample container in universal carrier block mounting aperture 74 will be outputted by detector 26 to system controller 350; whereby closed sample container sampling needle and needle drive assembly 28, sampling valve 30, and sample pump 32 will not be activated attendant sampling as described from micro-sample cup 160.

Immediately following sampling as described from micro-sample cup 160, carrier block 22 is again indexed as described to place open sample tube 132 in "sampling" position relative to probe 37, whereupon sampling of the sample liquid from liquid level adjusting device 134 in that tube by appropriate movement of probe 37 as described is accomplished; again with concomitant detection and outputting by detector 26 of the sample liquid identification data from label 156 on tube 132. Again, since tube 132 is an open sample container and does not include cap 140, no signal is outputted from detector 26 to controller 350 for activation of the closed tube sampling needle drive assembly 28 and related integrated sampler components as specified hereinabove with regard to sampling from open micro-sample cup 160.

Significantly, since both micro-sample cup 160 and liquid level adjusting device 134 function as described to retain the respective sample liquids contained therein at the same level relative to the upper surface of the universal carrier block 22, and thus at the same level relative to the inlet end 382 of the probe 37, the travel of which is precisely fixed as described, it will be clear that immersion of the probe to the same extent in the respective sample liquid sample contained in cup 160 and tube 132 is insured; thereby in turn insuring consistent and complete sample liquid aspiration by probe 37 from each of cup 160 and tube 132 for supply to sample liquid analysis system 270 with attendant maximization of the accuracy of the sample liquid analysis results as set forth hereinabove.

Immediately following sampling as described from tube 132, universal carrier block 22 is again indexed as described through appropriate actuation of shuttle drive motor 213 by system controller 350 on line 364 to place closed sample tube 152 in sampling position which, in this instance, is most relevantly defined in accordance with FIG. 12 wherein aligned sampling apertures 96 of the carrier block 22 and 196 of the drive shuttle 24 are disposed directly above sampling needle 46 and sleeve 228 and in direct alignment therewith. As carrier block 22 comes to rest in this position, the highly reflective surface of strip 141 on closed tube retainer end cap 140 is detected by detector 26, and an electrical signal indicative thereof outputted by the detector to system controller 350 on line 352 to key the integrated sampler 20 of my invention to the fact that sampling from a closed rather than open sample container must now be accomplished. As this occurs, system controller 350 activates probe drive motor 272 on line 366 to move probe 37 from the retracted position thereof of FIG. 1 directly over the carrier block 22 to the retracted position thereof of FIG. 1 directly over the sample liquid dispensing well 36.

Concomitantly, and making reference now to waveform 384 of FIG. 16, it will be seen that controller 350 activates solenoid 302 on line 356 to shift valve 294 and operate sleeve drive motor 234 to rapidly move sleeve 228 vertically upward into and through drive shuttle aperture 196 from the retracted to extended sleeve positions of the sleeve as respectively depicted in solid and phantom lines in FIG. 12. After a very brief time delay to insure that drive shuttle and carrier block sampling aperture alignment is correct and has permitted upward movement of the sleeve 228 as described, thus insuring that the way is clear for upward movement of the sampling needle 46, controller 350 activates solenoid 304 on line 358 to shift valve 296 as indicated by waveform 386 in FIG. 15 to operate sampling needle drive motor 242 to rapidly move the sampling needle 46 vertically upward into and through the aligned drive shuttle and carrier block sampling apertures 196 and 96 from the retracted to extended sampling needle positions as respectively depicted in solid and phantom lines in FIG. 12; with resultant piercing of the closed sample tube stopper 129 by the sampling needle, and the disposition of the sampling needle inlet end 408 in the sample liquid 410 contained in the sample tube 128. Since, as made clear by waveform 394 of FIG. 16, sample aspiration valve 278 is open as sampling needle 46 pierces closed tube stopper 129, equilibration of the pressure within closed sample tube 128 with the atmospheric pressure then prevailing in equilibration chamber 34, through the open needle end 408, conduit 38, sampling valve 30, volumetric conduit loop 48, sampling valve 30, and conduit 42 will then immediately occur, all in the manner and to the significant advantages with regard to insuring a full and consistent sample "pull" by needle 46 from closed sample tube 128 as disclosed in detail in my U.S. Pat. No. 4,756, 201.

Waveform 396 of FIG. 15 makes clear that pressure equilibration in closed sample tube is virtually immediately followed by the activation on line 376 by controller 350 of solenoid 290 to open sample aspiration control valve 280, thereby connecting equilibration chamber 34 and the open sampling needle end 408 to vacuum through conduit 52; whereupon aspiration of the sample liquid 410 from closed tube 128 is commenced through needle 46, conduit 38, sampling valve 30, volumetric loop conduit 48, sampling valve 30, conduit 42, the equilibration chamber 34, and conduit 52 which connects the same to vacuum as indicated on FIG. 1. However, as the leading edge of the thusly aspirated sample liquid 410 from closed sample tube 128 reaches sample liquid edge detector 54 in conduit 42, thus insuring that volumetric loop conduit 48, which is of course upstream of detector 54, is completely filled with a precisely predetermined quantity of the sample liquid 410, edge detector 54 outputs a signal indicative thereof to system controller 350; whereupon the controller activates solenoid on line 344 to close sample aspiration valve 278, as made clear by waveform 394 of FIG. 16, thereby discontinuing the aspiration of sample liquid 410 for closed sample tube 128.

Discontinuation as described of sample liquid aspiration from closed sample tube 128 is virtually immediately followed as illustrated by waveforms 384 and 386 of FIG. 15, by operation of system controller 350 to activate solenoids 302 and 304 on lines 356 and 358 to shift valves 294 and 296 to operate the sleeve and sampling needle drive motors to return the sleeve 28 and sampling needle 46 to the respective retracted positions thereof of FIG. 12; and by the activation by controller 350 of solenoid 328 on line 370 to shift valve 318 to operate rinse liquid pump 316 to commence the pumping of rinse liquid as illustrated by waveform 402 in FIG. 16. Concomitantly, system controller 350 activates solenoid 306 on line 360 to shift valve 298 as shown by waveform 390 in FIG. 16 to operate sampling valve drive motor 254 to rotate valve body member 252 relative to valve body member 250 to the non-illustrated relative positions thereof wherein the volumetric loop conduit 48 connects conduit 40 to conduit 44; thereby connecting sample pump 32 to dispensing well 36 through the sampling valve 30. As this is completed, system controller 350 activates solenoid 308 on line 362 to shift valve 300 as shown by waveform 390 in FIG. 15 to operate pump drive motor 260 to actuate sample pump 32 to pump a major portion, for example 250 ml of an available 300 ml, of the sample liquid 410 contained in volumetric loop conduit 48 therefrom through conduit 44 into bore 264 of the dispensing well 36, with particle trap 56 functioning to prevent the passage of any particulate matter as may be contained in the sample liquid into the dispensing well 36. As this is completed, system controller again activates solenoid 306 on line 360 to shift valve 306 as shown by waveform 390 in FIG. 16 to operate drive motor 254 to return the sampling valve 30 to the FIG. 1 position thereof; and, through solenoid 308, valve 300 and drive motor 260 deactivates and resets sample pump 32 as shown by waveform 392 in FIG. 16.

Immediately upon the deactivation of sample pump 32, controller 350 activates probe drive motor 272 on line 366 to move probe 37 from the retracted to extended positions thereof into the sample liquid 410 now supplied as described to the dispensing well 36 for sampling thereof and supply of a precisely predetemined sample liquid quantity to sample liquid analysis system 270 via conduit 271, and immediate return of the probe 37 to the retracted probe position. This makes clear that the integrated sampler 20 of my invention functions in full accordance with a stated object thereof to provide for sampling from closed sample containers through use of a relatively fragile sample analysis system probe which had heretofore been restricted to sampling from open sample containers, only. In addition, it will be clear that disposition as described of the sample dispensing well 36 at the same level relative to probe 37 as that of the open sample containers on universal carrier block 22 again maximizes the accuracy of the sample liquid analysis results as discussed in detail hereinabove.

Concomitantly with the return as described of the sampling valve 30 to the depicted sample liquid aspiration position thereof, controller 350 activates solenoid 284 on line 370 to open valve 274 as shown by waveform 388 to commence the flow of the rinse and surfactant liquids to the tubular passage 230 in sleeve 28 through conduit 58, and thus to the open tip 408 of the sampling needle 46; thereby thoroughly rinsing the exterior of the sampling needle of the residue of sample liquid 410, and lubricating with the surfactant liquid the sampling needle tip 48 and relevant exterior surface thereof to greatly facilitate the penetration thereby of the stopper of a succeeding closed sample container to minimize stopper particle generation and attendant contamination thereby of the sample liquid from that succeeding closed sample liquid container. System controller 350 then also activates peristaltic pump drive motor 338 on line 368 as shown by waveform 404 in FIG. 16 to operate pump rollers 334 and 336 to commence the flow of the isolation liquid from source 330 in conduits 332, 60 and 64 to the tubular sleeve passage 230 and the bore 264 of the dispensing well 36, respectively. In addition, system controller 350 then activates solenoid 288 on line 374 to reopen aspiration valve 278 as shown by waveform 394 in FIG. 16; and this, in conjuction with aspiration valve 280 which remains open as shown by waveform 392, results in the aspiration of the rinse and surfactant liquids from sleeve passage 230 through the open tip 408 of the sampling needle 46, the sampling needle, conduit 38, the internal passage in sampling valve 30 which now again connects conduit 38 to conduit 48, conduit 48, the internal passage in sampling valve 30 which now again connects conduit 48 to conduit 42, conduit 42, the equilibration chamber 34, and conduit 52, respectively, to vacuum and waste as indicated in FIG. 1. In addition, an extremely small quantity of the isolation liquid is flowed with the rinse and surfactant liquids from sleeve passage 230 through the entire sample liquid aspiration path as described; and this small isolation liquid quantity functions to replenish the thin isolation liquid layer which coats the same in accordance with the aspiration as described of sample liquids from preceding closed sample containers.

The particularly advantageous inclusion of significant quantities of air with the rinse and surfactant liquids which flow as described from sleeve passage 230 through the open sampling needle tip 408 to vacuum and waste as described is provided for by predetermining the level of the non-illustrated vacuum source to provide a total fluid flow rate QT which is significantly greater than the fluid flow rate QRST at which the rinse, isolation and surfactant liquids are supplied to sleeve passage 330 by rinse liquid pump 316. Thus, supply of the rinse and surfactant liquids as described to sleeve passage 230 will result in the same flowing upwardly and swirling around in that passage essentially to or slightly above the level of the open sampling needle tip 408 as clearly illustrated by the liquid flow arrows in FIG. 13, thereby very thoroughly cleansing from the relevant upper exterior portions 407 of the sampling needle 46 any residue of the sample liquid 410 from tube 128, the mixture at that level with the ambient air which is rapidly flowing into the open end 420 (FIGS. 12 and 13) of the tubular sleeve passage 230 below drive shuttle 24, and the rapid flow of the resultant rinse liquid-air mixture into the sampling needle 46 through open needle tip 408 for flow therefrom through the sampling needle and the entire sample liquid aspiration path to waste through conduit 52.

This admixture as described of the ambient air with the rinse liquid greatly enhances the scrubbing action thereof on the open needle tip 408 and interior passage 409 of the sampling needle 46, and greatly enhances the scrubbing action thereof on the hydrophobic isolation liquid-coated internal surfaces of conduit 38, the internal passages of sampling valve 30 which connects conduit 38 to volumetric loop conduit 48, volumetric loop conduit 48, and the internal passages of sampling valve 30 which connect volumetric loop conduit 48 to conduit 42; whereby will be immediately clear to those skilled in this art that virtually all residue of the sample liquid 410 from closed sample tube 128 will be removed therefrom by this rinse liquid-air mixture. Thus sample liquid carryover from the closed sample container sample liquid aspiration path upon the aspiration as described of a sample liquid from a succeeding closed sample container is virtually eliminated, or certainly reduced to levels well below those of highly stringent, contemporary clinical significance, for example, one part of a preceding sample liquid in 100,000 parts of a succeeding sample liquid. In addition, the use of ambient air as described along with the rinse and surfactant liquids greatly reduces the consumption by the integrated sampler 20 of my invention of the rinse and surfactant liquid solution with regard to sample liquid carryover minimization attendant sampling from closed sample containers, and this operates to render the sampler apparatus and method of my invention essentially independent of a high capacity or constantly flowing source of those liquids; it being noted in this regard that prior art samplers are known which require as much as 25 liters per hour of rinse 1. Also, this reduction as described in the amount of rinse liquid required significantly reduces the amount of rinse liquid which is of necessity left behind in the sample liquid flow path, and this in turn significantly reduces rinse liquid dilution of succeeding sample liquids.

Sample liquid edge detector 54 is electrically disabled by system controller 350 during sample liquid aspiration path rinse as described to prevent the actuation of sampling valve 30 by that detector upon rinse liquid passage through the latter.

Following particularly thorough rinsing of the closed sample container sample liquid aspiration path as described, solenoid 290 is activated by system controller 350 on line 376 to close valve 280 as shown by waveform 396 in FIG. 16, and solenoid 286 is activated by system controller 350 on line 372 to open sample liquid drain valve 276 as shown by waveform 398 in FIG. 16, thereby draining the remaining sample liquid 410 from the dispensing well 36 to vacuum and waste through conduit 44, sampling valve 30, and drain conduit 50. Shortly thereafter, controller 350 activates solenoids 286 and 292 on lines 372 and 378 to reclose valve 276 and open dispensing well rinse liquid control valve 282, as respectively shown by waveforms 398 and 400 in FIG. 16, thereby commencing the flow of rinse liquid from source 310 (FIG. 14) into the dispensing well 36 to fill the well bore 264 with rinse liquid to at least the level therein just occupied by the sample liquid 410 from closed sample tube 128. Controller 350 then activates solenoid 286 on line 372 to re-open drain valve 276 as shown by waveform 398 to flow the accumulated rinse liquid, followed by ambient air for drying, from well bore 264 through conduit 44, sample liquid particle trap 56, and sampling valve 30—thereby forcibly backflushing the same against the initial direction of flow of the sample liquid 410 therethrough—and drain conduit 50 to vacuum and waste. As a result, the hydrophobic isolation liquid-coated surfaces of dispensing well bore 264, conduit 44, and the relevant internal passages of sampling valve 30, are forcibly backflushed and cleansed of virtually all residue of sample liquid 410, to again virtually eliminate the contamination thereby of the sample liquid from a succeeding closed sample liquid container on universal carrier block 22.

Of course, the extremely small quantity of isolation liquid from source 330 (FIG. 14) supplied as previously described in detail with reference to waveform 404 of FIG. 16 to the bore 264 of the dispensing well 36, flows with this rinse liquid, although at a much lower flow rate, to replenish the extremely thin isolation liquid layer on the hydrophobic surfaces of dispensing well bore 264, conduit 44, and the relevant passages in sampling valve 30.

Operation of the integrated sampler 20 of my invention continues as described until sampling in turn from all sample liquid containers, be the same open or closed, on the universal carrier block 22 has been accomplished as described; it being clear to those skilled in this art that, in actual practice, a plurality, for example twenty, of the universal carrier blocks 22, each mounting six sample containers, would be provided and indexed in sequence by drive motor 213 under the control of system controller 350 vis-a-vis sample analysis system probe 37 as described to accomplish a full sampling "run".

Under all of the above circumstances, it will be clear that, for representative use as described with a hydrophobic sample analysis probe of the nature disclosed in U.S. Pat. No. 4,121,466 which also utilizes an isolation liquid for purposes of sample liquid carryover minimization, the new and improved integrated sampler 20 of my invention insures sample liquid carryover minimization from the point of sample liquid supply to the probe for aspiration, be it from a closed or open sample liquid container, virtually to the point of sample liquid analysis by the analysis system 270; thereby contributing very significantly to the overall accuracy of the sample liquid analysis results.

Various changes may of course be made in the apparatus and method of my invention as representatively disclosed herein without departing from the spirit and scope of that invention as defined in the appended claims.

What is claimed is:

1. In a sampling needle assembly for sampling from a sample liquid container which is closed by a pierceable stopper through use of a sampling needle which is moveable from a retracted needle position wherein the same does not pierce the container stopper to an extended needle position wherein the container stopper is pierced by the needle for withdrawal of sample liquid therefrom through the needle passage, the improvements comprising, sleeve means operatively associated with the sampling needle and moveable relative thereto from a retracted to an extended sleeve means position wherein said sleeve means insure that said sampling needle may be moved into said extended position thereof to pierce said container stopper without obstruction, and means operatively associated with said sleeve means and said sampling needle for preventing movement of said sampling needle into said extended position thereof unless said sleeve means have been moved into said extended sleeve means position.

2. In a sampling needle assembly for sampling in turn from sample liquid containers which are closed by pierceable stoppers through use of a sampling needle which is moveable from a retracted needle position wherein the same does not pierce a container stopper to an extended needle position wherein the container stopper is pierced by the needle for withdrawal of sample liquid therefrom through the needle passage, the improvements comprising, generally tubular sleeve means surrounding at least the end portion of said sampling needle and providing a passage therebetween, means operable following sample liquid withdrawal through said sampling needle passage and with said sampling needle returned to said retracted position thereof for introducing a rinse liquid to said sleeve means passage to surround at least the end portion of said sampling needle and remove sample liquid residue therefrom, and means for withdrawing said rinse liquid from said sleeve means passage through said sampling needle passage to remove sample liquid residue therefrom whereby, the contamination of a succeeding sample liquid from a succeeding closed sample container by sample liquid residue from the sampling needle end portion and sampling needle passage is minimized.

3. In a sampling needle assembly as in claim 2, the improvements further comprising, means for mixing said rinse liquid with ambient air upon the withdrawal of said rinse liquid from said sleeve means passage into said sampling needle whereby, the rinsing action of said rinse liquid on said sample liquid residue is enhanced, and the consumption of said rinse liquid is reduced.

4. In a sampling needle assembly as in claim 2, the improvements further comprising, means to introduce a surfactant with said rinse liquid into said sleeve means passage to lubricate the end portion of said sampling needle and facilitate the penetration thereby of the stopper of a succeeding closed sample liquid container whereby, the contamination of the sample liquid from the succeeding closed sample liquid container by particles of the container stopper is minimized.

5. In a sampling needle assembly as in claim 2 wherein, said sample and rinse liquids are aqueous liquids, and said assembly further comprises means forming a sample liquid flow passage operatively connected to said sampling needle passage for the flow of said sample and rinse liquids therefrom, the improvements further comprising, said sample liquid flow passage comprising hydrophobic surfaces, and means for introducing an isolation liquid with said liquid which selectively wets those hydrophobic surfaces to the substantial exclusion of the aqueous sample and rinse liquids for flow onto those surfaces thereby coating those surfaces with a layer of said isolation liquid which inhibits the adherence of the aqueous sample and rinse liquids thereto whereby, the contamination of succeeding aqueous sample liquids by the residue of preceding aqueous sample liquids is further minimized.

6. In a method for sampling from a sample liquid container which is closed by a pierceable stopper through use of a sampling needle which is moveable from a retracted needle position wherein the same does not pierce the container stopper to an extended needle position wherein the container stopper is pierced by the sampling needle for withdrawal of sample liquid therefrom through the sampling needle passage, and sleeve means which are operatively associated with said sampling needle and which are moveable from a retracted to an extended sleeve means position wherein said sleeve means insure that said sampling needle may be moved into said extended position thereof to pierce said container stopper without obstruction, the improvements comprising, the steps of, preventing the movement of said sampling needle into the extended position thereof unless said sleeve means have been moved into said extended sleeve means position.

7. In method for sampling in turn from sample liquid containers which are closed by pierceable stoppers through use of a sampling needle assembly comprising a sampling needle which moveable from a retracted needle position wherein the same does not pierce a container stopper to an extended needle position wherein the container stopper is pierced by the needle for withdrawal of sample liquid therefrom through the needle passage, and generally tubular sleeve means which surround at least the end portion of said sampling needle and provide a passage therebetween, the improvements comprising, the steps of, introducing a rinse liquid to said sleeve means passage to surround at least the end portion of said sampling needle following sample liquid withdrawal through said needle passage and with said sampling needle returned to the retracted position thereof, thereby removing sample liquid residue from said sampling needle end portion, and withdrawing said rinse liquid from said sleeve means passage through said sampling needle passage, thereby removing sample liquid residue from said sampling needle passage, whereby the contamination of a succeeding sample liquid from a succeeding closed sample container by sample liquid residue from the sampling needle end portion and sampling needle passage is minimized.

8. In a method as in claim 7, the improvements further comprising, the steps of, mixing said rinse liquid with ambient air upon the withdrawal of said rinse liquid from said sleeve means passage into said sampling needle passage whereby, the rinsing action of said rinse liquid on sample liquid residue is enhanced, and the consumption of said rinse liquid reduced.

9. In a method as in claim 7, the improvements further comprising, the steps of, introducing a surfactant with said rinse liquid into said sleeve means passage to lubricate the end portion of said sampling needle and facilitate the penetration thereby of the stopper of a succeeding closed sample liquid container whereby, the contamination of the sample liquid from the succeeding closed sample liquid container by particles of the container stopper is minimized.

10. In a method as in claim 7 wherein, said sample and rinse liquids are aqueous, and sampling needle assembly further comprises means forming a sample liquid flow passage operatively connected to said sampling needle passage for the flow of said sample and rinse liquids therefrom and having hydrophobic surface, the improvement further comprising, introducing an isolation liquid with said rinse liquid which selectively wets those hydrophobic exclusion of the aqueous sample and rinse liquids for flow onto those surfaces to coat the same with a layer of said isolation liquid which inhibits the adherence of the aqueous sample and rinse liquids thereto whereby, the contamination of succeeding aqueous sample liquids by the residue of preceding aqueous sample liquids is further minimized.

* * * * *